(12) United States Patent
Triplett et al.

(10) Patent No.: US 7,141,395 B2
(45) Date of Patent: Nov. 28, 2006

(54) BIOLOGICAL CONTROL OF CROWN GALL DISEASE

(75) Inventors: Eric W. Triplett, Middleton, WI (US); Thomas C. Herlache, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 306 days.

(21) Appl. No.: 09/927,616

(22) Filed: Aug. 10, 2001

(65) Prior Publication Data

US 2002/0090354 A1 Jul. 11, 2002

Related U.S. Application Data

(60) Provisional application No. 60/224,929, filed on Aug. 11, 2000.

(51) Int. Cl.
- C12P 21/04 (2006.01)
- C12N 1/20 (2006.01)
- A01N 63/00 (2006.01)
- A61K 48/00 (2006.01)

(52) U.S. Cl. ............... 435/71.3; 435/252.2; 435/252.3; 424/93.2; 424/93.4

(58) Field of Classification Search ............. 435/252.2, 435/252.3, 320.1, 71.3; 536/23.1; 424/93.1, 424/93.2, 93.4, 98.4
See application file for complete search history.

(56) References Cited

FOREIGN PATENT DOCUMENTS

| EP | 0313333 A2 | 4/1989 |
|---|---|---|
| WO | WO 90/15138 | 12/1990 |
| WO | WO 98/50564 | 11/1998 |

OTHER PUBLICATIONS

See printed out screens from www.life.umd.edu/classroom/biosci42, Jan. 30, 2004.*
Spaink, et. al. in The Rhizobiaceae, 1998, Kluwer Publishers, Netherlands, p. xiii.*
Potrykus, Gene Transfer to Cereals: An Assessment, 1990, Biotechnology, 8(6): 535-542 p. 538, col. 2, 3rd full .¶.*
Breil et al, NCBI Accession No. L06719, locus RHMTFXA2G, Aug. 4, 1993.*
Burr et. al., Annu. Rev. Phytopathol. 1999, vol. 37, pp. 37-53.*
Herlache et. al., BMC Biotechnology, 2002, vol. 2, No. 2 pp. 1-7.*
Burr et. al., Phytopathology 1997.*
Samac et. al., Alpplied Soil Ecology, vol. 22, 2003, pp. 55-66.*
Schmiedeknecht. et. al., 2001, J. Plant Diseases and Protection, vol. 108, No. 5, pp. 500-512.*
Burr et. al., Am. J. Enol. Vitic. 1994, vol. 45, p. 213.*
Annual Review of Phytopathology, Sep. 1999, vol. 37, pp. 53-80.*
Herlache and Triplett, 2002, BMC Biotechnology vol. 2, p. 2.*
Burr et. al., Phytopahtology, 1997, vol. 87, No. 7, pp. 705-711.*
Samac et. al., Applied Soil Ecology, 2003, vol. 22, No. 1, pp. 55-66.*
Schmiedeknecht et. al., Zeitschrift fuer Pflanzenkrankheiten und Pfhlansezschutz, 2001, vol. 108 No. 5, pp. 500-512.*
Breil BT, Ludden PW, Triplett EW. "DNA sequence and mutational analysis of genes involved in the production and resistance of the antibiotic peptide trifolitoxin." *J Bacteriol*, (Jun. 1993) 175(12):3693-702 (Abstract).
Chen D, Zhou J. "The expression and stability of tfx gene in Sinorhizobium fredii H12-2." *Weishengwuxue Zazhi*, (1998) 18:7-12 (Abstract).
Herlache TC, Triplett E. "Trifolitoxin production enhances biological control of A. vitis-induced crown gall." *Phytopathology*, (2000) 90:6, Suppl., S35 (Abstract).
Robleto EA, Kmiecik K, Oplinger ES, Nienhuis J, Triplett EW. "Trifolitoxin Production Increases Nodulation Competitiveness of *Rhizobium etli* CE3 under Agricultural Conditions." *Appl Environ Microbiol*, (Jul. 1, 1998) 1;64(7):2630-3.
Triplett EW, Breil BT, Splitter GA. "Expression of tfx and sensitivity to the rhizobial peptide antibiotic trifolitoxin in a taxonomically distinct group of alpha-proteobacteria including the animal pathogen *Brucella abortus*." *Appl Environ Microbiol*, (Nov. 1994) 60(11):4163-6 (Abstract).
Triplett EW. "Isolation of genes involved in nodulation competitiveness from *Rhizobium leguminosarum* bv Trifolii T24." *PNAS*, (1998) 85:3810-3814 (Abstract).
Triplett, et al., "Expression of *tfx* and Sensitivity to the Rhizobial Peptide Antibiotic Trifolitoxin in a Toxonomically Distinct Group of α-Proteobacteria Including the Animal Pathogen *Brucella abortus*," *Applied and Environmental Microbiology*, 60(11) :4163-66. (1994) .

* cited by examiner

*Primary Examiner*—David T. Fox
*Assistant Examiner*—Georgia Helmer
(74) *Attorney, Agent, or Firm*—Quarles & Brady LLP

(57) ABSTRACT

The present invention provides a method for controlling crown gall disease in plants using an effective quantity of α-proteobacteria that produces trifolitoxin (TFX). The present invention also provides a biocontrol agent for use in the above method, and a plant coated with the biological control agent. The biocontrol agent is characterized as a biologically pure culture of an α-proteobacteria strain that produces TFX, or an α-proteobacteria strain genetically engineered to produce TFX. The α-proteobacteria strain employed may include any one of the many strains of *Agrobacterium* capable of producing crown galls, including *Agrobacterium vitis* and, in particular, *A. vitis* F2/5. The α-proteobacteria strain employed may be genetically engineered to produce TFX by introducing a genetic construct into the *Agrobacterium* so as to cause the *Agrobacterium* to carry and express the tfx operon from *Rhizobium*. The bacteria may also be genetically engineered to produce TFX by introducing a pT2TFXK plasmid into the *Agrobacterium*. The biocontrol agent may also be the strain *Agrobacterium vitis* F2/5 (pT2TFXK), ATCC Patent Deposit Designation PTA-2356.

10 Claims, 2 Drawing Sheets

SEQUENCE LISTING

```
<160> NUMBER OF SEQ ID NOS: 9

<210> SEQ ID NO 1
<211> LENGTH: 7142
<212> TYPE: DNA
<213> ORGANISM: Rhizobium leguminosarum bv. trifolii
<220> FEATURE:
<221> NAME/KEY: CDS
<222> LOCATION: (597)..(722)
<223> OTHER INFORMATION: tfxA coding sequence
<221> NAME/KEY: CDS
<222> LOCATION: (794)..(1912)
<223> OTHER INFORMATION: tfxB coding sequence
<221> NAME/KEY: CDS
<222> LOCATION: (2982)..(4229)
<223> OTHER INFORMATION: tfxD coding sequence
<221> NAME/KEY: CDS
<222> LOCATION: (4968)..(5741)
<223> OTHER INFORMATION: tfxF coding sequence
<221> NAME/KEY: CDS
<222> LOCATION: (5996)..(6778)
<223> OTHER INFORMATION: tfxG coding sequence

<400> SEQUENCE: 1
cgcgtaaaag acacgagcag tctccgtaga ccataagaag cttttagagc agccaacgca      60
tagcagccgc ttttctaaag ctgctagcag cttggtgctt attccttggt agcgtacgat     120
tggatcgata tacaaaagtg taatctcgcc actaacaaga gccgatccga ctcctcttac     180
tagtccggca accttagctg taagaaatat tgagtgcggg ttgtcaatcc acatcgatac     240
gtttgctgcg gtcttgttct ccaaccactc atctatttcg gcagaatttc cgtgatggtc     300
agccaagcaa agttctgcga ttgatcgccg caatacacgg gcgcagtcgg cggcatctat     360
cgccgaagcg tcaccaattt ccgcagcgag gttttctcgc tgcataattt ttttctttcc     420
tgaatcgatc attagttgtg tttttttgttg ctctcgacgt attttgcaacc gtttgattcg    480 attgcgtatt tgtcaaaata ctccatatga ttgcatttt taaaagacaa gataggctca      540
catttgtcag caaatgactg ctggcaaacc ccaatcgcta aatgaggtgt tgttgc atg      599
                                                                Met
                                                                  1 gat aac aag gtt gcg aag aat gtc gaa gtg aag aag ggc tcc atc aag        647
Asp Asn Lys Val Ala Lys Asn Val Glu Val Lys Lys Gly Ser Ile Lys
        5                   10                  15 gcg acc ttc aag gct gct gtt ctg aag tcg aag acg aag gtc gac atc       695
Ala Thr Phe Lys Ala Ala Val Leu Lys Ser Lys Thr Lys Val Asp Ile
    20                  25                  30 gga ggt agc cgt cag ggc tgc gtc gct taagtgaaca tccggcgggt              742
Gly Gly Ser Arg Gln Gly Cys Val Ala
        35                  40 gcggcaaacg tacccgccac ttatgccctc gctttcaacg ggatgtttcg c atg gac       799
```

|  |  |  |  |  |  |  |  |  |  |  |  |  |  |  |  |
|---|---|---|---|---|---|---|---|---|---|---|---|---|---|---|---|
|  |  |  |  |  |  |  |  |  |  |  |  |  |  | Met | Asp |

```
ttc gtc caa cga ttc gta atc gac cgc tct ttc cac ctc cgc tac tac     847
Phe Val Gln Arg Phe Val Ile Asp Arg Ser Phe His Leu Arg Tyr Tyr
 45                  50                  55                  60 agc ctc gac gcc tat cta tat cgc gca gtt gac cag gtc gcc tgg gac     895
Ser Leu Asp Ala Tyr Leu Tyr Arg Ala Val Asp Gln Val Ala Trp Asp
                 65                  70                  75 gca gac atc act cac aat cgc cta ttt tgg gac att tgg tca gca ttc     943
Ala Asp Ile Thr His Asn Arg Leu Phe Trp Asp Ile Trp Ser Ala Phe
             80                  85                  90 atg cag ccg aga agt ctg gta gac gct gtt gag acg cta tcc gat tac     991
Met Gln Pro Arg Ser Leu Val Asp Ala Val Glu Thr Leu Ser Asp Tyr
         95                 100                 105 gat ccc gac gaa gtg gcc gca gca atc gaa ggc atg tgc gag tcg ggc    1039
Asp Pro Asp Glu Val Ala Ala Ala Ile Glu Gly Met Cys Glu Ser Gly
    110                 115                 120 atc atc gaa ccg gtg ggc ttg aaa gac cgc caa ttt gat cct ttg acg    1087
Ile Ile Glu Pro Val Gly Leu Lys Asp Arg Gln Phe Asp Pro Leu Thr
125                 130                 135                 140 gta gag ctg tca cat gtg cca cag gca tgg gat tat cac ctg gtc tca    1135
Val Glu Leu Ser His Val Pro Gln Ala Trp Asp Tyr His Leu Val Ser
                145                 150                 155 agt cgc atc gac tgg atc aat tat ctg gat ggg aag gac gtt aaa cgc    1183
Ser Arg Ile Asp Trp Ile Asn Tyr Leu Asp Gly Lys Asp Val Lys Arg
            160                 165                 170 cag gac ctt gaa caa atg gac aag cat ttg tcg gag gag gct gtt ccg    1231
Gln Asp Leu Glu Gln Met Asp Lys His Leu Ser Glu Glu Ala Val Pro
        175                 180                 185 tcg aat ttt cac aag gcc gcc aac tct cga ccg aaa tat gat ttg cca    1279
Ser Asn Phe His Lys Ala Ala Asn Ser Arg Pro Lys Tyr Asp Leu Pro
    190                 195                 200 agt tta gtg ccg ctg aca gcg ttc gaa ttc aat aac tcg gcg tcc gtc    1327
Ser Leu Val Pro Leu Thr Ala Phe Glu Phe Asn Asn Ser Ala Ser Val
205                 210                 215                 220 gca ttc ggt cat gag aag gca ccg ctt ccg aac gaa ctg tcg ctc gat    1375
Ala Phe Gly His Glu Lys Ala Pro Leu Pro Asn Glu Leu Ser Leu Asp
                225                 230                 235 ata atc aca ttg ctc ctc aac tat gcg gcc gca aag acg gat acc gtc    1423
Ile Ile Thr Leu Leu Leu Asn Tyr Ala Ala Ala Lys Thr Asp Thr Val
            240                 245                 250 aac atg tat gcc act ggc gag cat ctg cga aag gcc gtc cca tcc gga    1471
Asn Met Tyr Ala Thr Gly Glu His Leu Arg Lys Ala Val Pro Ser Gly
        255                 260                 265 gga gcg cga cac ccc atc gaa ttc tac gtg gtt gtc ggc gat gag att    1519
Gly Ala Arg His Pro Ile Glu Phe Tyr Val Val Val Gly Asp Glu Ile
    270                 275                 280 gca ggt atc gaa gct ggc gta tat cac tac aat gtt cgc cat cat cgg    1567
Ala Gly Ile Glu Ala Gly Val Tyr His Tyr Asn Val Arg His His Arg
285                 290                 295                 300 ctc gat gct atc gaa ata gcg tcc acc tca ttg aaa gca ctg caa gag    1615
Leu Asp Ala Ile Glu Ile Ala Ser Thr Ser Leu Lys Ala Leu Gln Glu
                305                 310                 315 gca agc tca gtg ctg ccc cga tca cgg tca aaa ccg ttc ggc ttt gct    1663
Ala Ser Ser Val Leu Pro Arg Ser Arg Ser Lys Pro Phe Gly Phe Ala
            320                 325                 330 ttc att cat aca tgt cgg ttc gag cga agt atg ttt cgg tac cgc gaa    1711
Phe Ile His Thr Cys Arg Phe Glu Arg Ser Met Phe Arg Tyr Arg Glu
        335                 340                 345 ccg cga agc tac cgt gtg atg cag ttt gat ctt ggg cat atc cat gcc    1759
```

|  |  |
|---|---|
| Pro Arg Ser Tyr Arg Val Met Gln Phe Asp Leu Gly His Ile His Ala<br>    350                          355                    360 |  |
| aac gag gtt ttg gct gcc aaa atc ctc ggc ctc gat ttc agt gaa acc<br>Asn Glu Val Leu Ala Ala Lys Ile Leu Gly Leu Asp Phe Ser Glu Thr<br>365                         370                      375                   380 | 1807 |
| ttt tct gtg ccg gaa agc ata gtt gag agc gtc ttg acg ctc gat ccg<br>Phe Ser Val Pro Glu Ser Ile Val Glu Ser Val Leu Thr Leu Asp Pro<br>                  385                      390                   395 | 1855 |
| ttc atc gag tcc gcg atg tca gcc ttt gtc gtc cac aga cac gag aac<br>Phe Ile Glu Ser Ala Met Ser Ala Phe Val Val His Arg His Glu Asn<br>              400                      405                   410 | 1903 |
| cac cat gat tgaactgcgc ccgcttctcc aactgaatct tgaagatgga<br>His His Asp<br>            415 | 1952 |
| atcccggtcc tcaaagacct cctgaccgcc gacagctttt ccttcaccga tgttgaactc | 2012 |
| ttgcggtaca ttccagccat tgccaagaac accccgccc agactcggga tttggctgcc | 2072 |
| tctgttgctg atgcgctgga tgttgaccaa accaccgcgc tcgcagccat cgaagcattg | 2132 |
| gttgagcttg tcttttggt gccatccgcg tcgatctcct cgcagaaggc agggatccag | 2192 |
| ttgtgggtgg ataagggatg ggtggacgca ctgatcctgc atttcgcgag cagaaatctc | 2252 |
| aattataatg acgatccaat tgaatttggc gggttggagg atatcaaaag ctatcccgaa | 2312 |
| ccgatggaat cgaagcgtag gaaacgcggc accgccacgc gattggtcaa gccgtcccgg | 2372 |
| gagctggcag ctgcagtcat actggacggg ctcatgaaca ggcgctcgtt caaacccttc | 2432 |
| acacgcaaac aactgtcgat caccgaggtc agcgagatac tttggtttgg gaacctctat | 2492 |
| gcgcgagaac gcgcggtcat cgctgaaaat cgtgacttcg agtctcctcg cgatatagct | 2552 |
| ttcgacagcg ccttctcagc gttgtccacc tttgttgtca catatggaca gatcgattgg | 2612 |
| caggatggct cgttgccacc cggagtctat cgttacaatg tcgtcaatca cgaacttgaa | 2672 |
| gcaatcagag ccggtgattt caagctggac atggcaaaac tcgctatcgg tcagagtcgg | 2732 |
| gcttcgagcg ggctattcac gtttgtgatc tgcggcgatt tgaagtcata cacatcgcgg | 2792 |
| tacaggcacg agcggagcta ccgcaatctg ctgatcaaca cctcacagct cgcccaattc | 2852 |
| tatttgaccc tcgcaacgat caacgacttc aacacctttc tcacgcccgc catccacgat | 2912 |
| gagaaaatgc atctgtttct tgaagcggag gacgacctcc cgctttatct cgtcacggca | 2972 |
| ggctagagc atg agc gac gaa aac cag cat ggg ttc tat cgg act tcg ttc<br>            Met Ser Asp Glu Asn Gln His Gly Phe Tyr Arg Thr Ser Phe<br>                              420                      425 | 3023 |
| gaa tac gca tcg atc agt tgg cgg aga atg att ccc aat gtg gct gac<br>Glu Tyr Ala Ser Ile Ser Trp Arg Arg Met Ile Pro Asn Val Ala Asp<br>430                       435                      440                   445 | 3071 |
| act atc gtc gtc acg ctc atc ggc gct act gca ctt cag gtg gcg tca<br>Thr Ile Val Val Thr Leu Ile Gly Ala Thr Ala Leu Gln Val Ala Ser<br>                  450                      455                   460 | 3119 |
| aat gtt ctg atc acg ata ctg acc ctc aat atc gct ttt ctg aac ttt<br>Asn Val Leu Ile Thr Ile Leu Thr Leu Asn Ile Ala Phe Leu Asn Phe<br>                465                      470                   475 | 3167 |
| tgc tcg ctt atc tgc atg cac aat ctg aaa aga ggg gca aag gcc gac<br>Cys Ser Leu Ile Cys Met His Asn Leu Lys Arg Gly Ala Lys Ala Asp<br>            480                      485                   490 | 3215 |
| gta ttt gct gca atc gtc cgc gct gct tgc atg atg atc ggg gtc tac<br>Val Phe Ala Ala Ile Val Arg Ala Ala Cys Met Met Ile Gly Val Tyr<br>495                       500                       505 | 3263 |
| ctg gcg ctt atc gcg gtc tcc gtc gcc acc ctc gaa ggt gca ccg cgt<br>Leu Ala Leu Ile Ala Val Ser Val Ala Thr Leu Glu Gly Ala Pro Arg | 3311 |

-continued

```
              510                 515                 520                 525
acc caa acc att gct ttc ata gca ctg tct gcg ctc cgg ccg ttt gtg         3359
Thr Gln Thr Ile Ala Phe Ile Ala Leu Ser Ala Leu Arg Pro Phe Val
                    530                 535                 540 gct gga tgg aat gct tac tgt gcg gag gtt ttt ttc gcc cag gga aaa         3407
Ala Gly Trp Asn Ala Tyr Cys Ala Glu Val Phe Phe Ala Gln Gly Lys
            545                 550                 555 cga caa att gtg cga agc gtc atc acg aga tcg tcg ctg atc tat gca         3455
Arg Gln Ile Val Arg Ser Val Ile Thr Arg Ser Ser Leu Ile Tyr Ala
                560                 565                 570 gga gtt aat ctg ctc ttt gtc ggg ctg tcg cat ttc gct ggc act caa         3503
Gly Val Asn Leu Leu Phe Val Gly Leu Ser His Phe Ala Gly Thr Gln
        575                 580                 585 aat tcg atc ata tcg ctt ctc atc ggc gta tat ctt gct ctc ttc cac         3551
Asn Ser Ile Ile Ser Leu Leu Ile Gly Val Tyr Leu Ala Leu Phe His
590                 595                 600                 605 aac gcc ctg gcc tac gcc aga atc ctg ccg acc gaa tgg agg ttc agt         3599
Asn Ala Leu Ala Tyr Ala Arg Ile Leu Pro Thr Glu Trp Arg Phe Ser
                    610                 615                 620 cgc cag gat ttg aag gat gtc ttc tca ctt cgg aag ctt gat ctg gtc         3647
Arg Gln Asp Leu Lys Asp Val Phe Ser Leu Arg Lys Leu Asp Leu Val
            625                 630                 635 gga atc ggg gca ggg ctt tct gcg tct ttt atc aac atg ctc gaa atg         3695
Gly Ile Gly Ala Gly Leu Ser Ala Ser Phe Ile Asn Met Leu Glu Met
        640                 645                 650 ggg ttt ctt gca tta gtt ggg tgg gtg gtg gca gca aag ttt ccg caa         3743
Gly Phe Leu Ala Leu Val Gly Trp Val Val Ala Ala Lys Phe Pro Gln
655                 660                 665 atc gcg gtt ttt tat ttc ccg ttt ttc act ttg gtg gaa ttg acg agc         3791
Ile Ala Val Phe Tyr Phe Pro Phe Phe Thr Leu Val Glu Leu Thr Ser
670                 675                 680                 685 gga ctt gcg att ggg ctt gga cgc tca gtc acc gaa cgt ttg att acg         3839
Gly Leu Ala Ile Gly Leu Gly Arg Ser Val Thr Glu Arg Leu Ile Thr
                    690                 695                 700 ccg cgc ccg ttt ccc cgg ctg cac gtc ttg atc gcc gtt tac agc acg         3887
Pro Arg Pro Phe Pro Arg Leu His Val Leu Ile Ala Val Tyr Ser Thr
            705                 710                 715 tat tcg ttg ctc tgc ttc ttg atc tac gtt gga tta ata ggt gtg agc         3935
Tyr Ser Leu Leu Cys Phe Leu Ile Tyr Val Gly Leu Ile Gly Val Ser
        720                 725                 730 aat cgg gac ata ttt gct ctc ccg ctg tcg ctt gcc gga ttg gcg cta         3983
Asn Arg Asp Ile Phe Ala Leu Pro Leu Ser Leu Ala Gly Leu Ala Leu
735                 740                 745 ctt ttc ctg atc tgc gac ggg ctg cag ctt gtg gtt cgg gga tat acg         4031
Leu Phe Leu Ile Cys Asp Gly Leu Gln Leu Val Val Arg Gly Tyr Thr
750                 755                 760                 765 ctc gcc aaa gct gac gga ggc aag ctc acg cat ctc agc gcc att gca         4079
Leu Ala Lys Ala Asp Gly Gly Lys Leu Thr His Leu Ser Ala Ile Ala
                    770                 775                 780 tac cta gcc tct gga gtg atc ctc gcg ctg gcg gcc gtc ttg ggc tcg         4127
Tyr Leu Ala Ser Gly Val Ile Leu Ala Leu Ala Ala Val Leu Gly Ser
            785                 790                 795 gtt caa gcg ttg gcc atc gct ttg gtc ttg gga ccg ctg ttc ctt gca         4175
Val Gln Ala Leu Ala Ile Ala Leu Val Leu Gly Pro Leu Phe Leu Ala
        800                 805                 810 atc tcc att ccc gcc gtt caa agt cga act gcc cta aat gca cta ccg         4223
Ile Ser Ile Pro Ala Val Gln Ser Arg Thr Ala Leu Asn Ala Leu Pro
815                 820                 825 aac aga taaaccgaaa gtattcgtaa ccgactccgg caggtttgtt gctgactgcc          4279
Asn Arg
```

```
Asn Arg
830 agataattct gcttggtcgc aagatcatat gtacgggaac cgatcttcag tacgagattg    4339 cggttgcaaa agcaaagtct gagcttgcgg agaggatcgc gtttgcatca ccagacgcct    4399 tcaatgcgcg agtgacgcgg gttgcaaggc gtctcatgct cgaagctacc aatgccttca    4459 acagagaatc cgtcaccctg ccgttgagct tgttcgtaac gcggccacat ctgtgctgga    4519 tgcgcggcaa caactccaca ggatttgccg cacatccccg gcgcaaggca gcaattgaac    4579 acgcggtcaa tgaggtttta gagcgcggct ggaacgctcg gtttcgacga gatcagcagt    4639 ctcttcttaa gttggccacg atccgacgag acggttcaac agcttgggta cacgaatcga    4699 ggctccgcca ggtttcctac tgcttggcca acgcccgtgt tgcgggacat gtcggttggg    4759 gttccgcagt tcgcagaacg accgaagcgg cagtggaagc tgcaactagt gaagcccatg    4819 cgatgagtgc gtcggggcag gattacggtc gcggcggaac cggcgtgtcg gagcttccct    4879 cgcaacacga ccaaatcgcg tttgtcgaga ggcagccggt gcgcatcgat gacgtcactc    4939 attacgtgat acaggcggtg agttattc atg aga gca agc aaa aca ccg atc        4991
                                Met Arg Ala Ser Lys Thr Pro Ile
                                                        835 ttg ata aac ggc tct ccg tgg ttg tta gat ttc cgt cgg cgg tca agc    5039
Leu Ile Asn Gly Ser Pro Trp Leu Leu Asp Phe Arg Arg Arg Ser Ser
840             845                 850                 855 cga gaa ttc gat tgg gaa att gcc gaa cat cta gag gtg ccc gaa gca    5087
Arg Glu Phe Asp Trp Glu Ile Ala Glu His Leu Glu Val Pro Glu Ala
                860                 865                 870 tat ttt cag gcg tat gac ccg cta aca act tgg ttc gag tgg ttt tct    5135
Tyr Phe Gln Ala Tyr Asp Pro Leu Thr Thr Trp Phe Glu Trp Phe Ser
    875                 880                 885 cgg atc ggc tat cga gat tac acc gat gct gag gcc gaa att gag cga    5183
Arg Ile Gly Tyr Arg Asp Tyr Thr Asp Ala Glu Ala Glu Ile Glu Arg
890                 895                 900 gat gcc gag gaa aat gta cgg cag cac caa gtt tcc gtt caa ccc gat    5231
Asp Ala Glu Glu Asn Val Arg Gln His Gln Val Ser Val Gln Pro Asp
    905                 910                 915 ctc acg ctg acc cag cgc cta tcg agc gaa ggc tcg atc cag ctt cca    5279
Leu Thr Leu Thr Gln Arg Leu Ser Ser Glu Gly Ser Ile Gln Leu Pro
920                 925                 930                 935 gtt ccg ttc cta aaa acg gcc gat caa ttt tgt atc ttg tcg tcg ctc    5327
Val Pro Phe Leu Lys Thr Ala Asp Gln Phe Cys Ile Leu Ser Ser Leu
                940                 945                 950 ctg tac gcc ggt ttt gga gtg gtt gag acg cgg aaa ttc cac ggt gac    5375
Leu Tyr Ala Gly Phe Gly Val Val Glu Thr Arg Lys Phe His Gly Asp
            955                 960                 965 acg atc ttc cta aaa aac gta cct tcg gtt gga gcg cgt cac ggc att    5423
Thr Ile Phe Leu Lys Asn Val Pro Ser Val Gly Ala Arg His Gly Ile
        970                 975                 980 gag gct tat gtt tcc ctg gat gac ggg cgc tat tat tac gac tgt gag    5471
Glu Ala Tyr Val Ser Leu Asp Asp Gly Arg Tyr Tyr Tyr Asp Cys Glu
985                 990                 995 cag cat cgg ttg ttt tcc gca ggc tat cgg ggt gat cta cgg agc ggt    5519
Gln His Arg Leu Phe Ser Ala Gly Tyr Arg Gly Asp Leu Arg Ser Gly
1000            1005                1010                1015 cag atc gat atc gta ttt cgg cct gag gta tac atg tgg cgt tat caa    5567
Gln Ile Asp Ile Val Phe Arg Pro Glu Val Tyr Met Trp Arg Tyr Gln
            1020                1025                1030 acc gct gcc tgt ctt gcc gat gtc tac ctc gac ctt ggc cac ata tta    5615
Thr Ala Ala Cys Leu Ala Asp Val Tyr Leu Asp Leu Gly His Ile Leu
```

-continued

```
                1035                1040                1045
ggt act cta tcg atg gtg gcg tcc ctc tat gac acg tct atc acg agc      5663
Gly Thr Leu Ser Met Val Ala Ser Leu Tyr Asp Thr Ser Ile Thr Ser
        1050                1055                1060 cgc tct gca gaa gcc gct cct gta gac ttg atc aat gcg gtg cat ctc      5711
Arg Ser Ala Glu Ala Ala Pro Val Asp Leu Ile Asn Ala Val His Leu
    1065                1070                1075 cag cga ata gcc gtt gat gga ttt aat cca taggcgcagg acgggaatgc        5761
Gln Arg Ile Ala Val Asp Gly Phe Asn Pro
1080                1085 ctgcgaactg aagaaggccg acgatccgtt tttctcttga tgaacgccgt cggccagtcg    5821
tccgttttgg gccgtaagcg ctgacccagc ggcggcaaca gcgaccgtgt ctttatggcg    5881
gcttgccaac gacaggagcg aggcccttga ggtgcagaaa tcgttgccgg ggggcgaagg    5941
ctgaaaggta aacgcgccgc ttgtggtgct actaatggaa tccaggtggg tgcc atg      5998
                                                              Met
                                                              1090 aat gat gag att tgc ctg aca ggt ggc gga cga acg act gtc acg cgg      6046
Asn Asp Glu Ile Cys Leu Thr Gly Gly Gly Arg Thr Thr Val Thr Arg
                1095                1100                1105 cgc ggc gga gtc gtg tat cgc gaa ggc ggc ccg tgg tca tca acc gtc      6094
Arg Gly Gly Val Val Tyr Arg Glu Gly Gly Pro Trp Ser Ser Thr Val
        1110                1115                1120 att tcg ctc ctg cgg cat ctg gaa gcc tct ggc ttc gct gaa gct cct      6142
Ile Ser Leu Leu Arg His Leu Glu Ala Ser Gly Phe Ala Glu Ala Pro
    1125                1130                1135 tcc gtt gtc ggc acc ggt ttc gat gag cgc ggc cgg gag aca tta tcg      6190
Ser Val Val Gly Thr Gly Phe Asp Glu Arg Gly Arg Glu Thr Leu Ser
1140                1145                1150 ttt atc gag ggt gag ttt gtt cac cca ggc cct tgg tcg gag gag gct      6238
Phe Ile Glu Gly Glu Phe Val His Pro Gly Pro Trp Ser Glu Glu Ala
1155                1160                1165                1170 ttt ccg caa ttt gga atg atg ttg cgg cga ctg cac gat gcc acc gcc      6286
Phe Pro Gln Phe Gly Met Met Leu Arg Arg Leu His Asp Ala Thr Ala
                1175                1180                1185 tcg ttc aaa cct ccc gaa aac tcg atg tgg cgc gat tgg ttc ggg cgt      6334
Ser Phe Lys Pro Pro Glu Asn Ser Met Trp Arg Asp Trp Phe Gly Arg
        1190                1195                1200 aac ctc ggt gag ggt caa cac gta ata gga cac tgc gac aca ggc cca      6382
Asn Leu Gly Glu Gly Gln His Val Ile Gly His Cys Asp Thr Gly Pro
    1205                1210                1215 tgg aac att gtt tgc cgg tca gga ttg cct gtc ggg ttg ata gat tgg      6430
Trp Asn Ile Val Cys Arg Ser Gly Leu Pro Val Gly Leu Ile Asp Trp
1220                1225                1230 gag gtg gct ggg cct gtc agg gcg gat atc gaa ttg gcc cag gct tgt      6478
Glu Val Ala Gly Pro Val Arg Ala Asp Ile Glu Leu Ala Gln Ala Cys
1235                1240                1245                1250 tgg ctg aat gcc cag ctc tac gat gac gac att gcg gag agg gtc gga      6526
Trp Leu Asn Ala Gln Leu Tyr Asp Asp Asp Ile Ala Glu Arg Val Gly
                1255                1260                1265 tta ggc tct gtg acc atg aga gcg cat caa gtt cgc ctg ctg ctt gac      6574
Leu Gly Ser Val Thr Met Arg Ala His Gln Val Arg Leu Leu Leu Asp
        1270                1275                1280 ggc tat ggt ctg tct cgg aag caa cgc ggc ggc ttc gtc gac aag cta      6622
Gly Tyr Gly Leu Ser Arg Lys Gln Arg Gly Gly Phe Val Asp Lys Leu
    1285                1290                1295 atc acg ttc gca gtt cac gat gcg gcc gag cag gcg aaa gag gcg gct      6670
Ile Thr Phe Ala Val His Asp Ala Ala Glu Gln Ala Lys Glu Ala Ala
1300                1305                1310
```

```
gtc acg cca gag tcg aac gat gcg gaa ccg cta tgg gca att gcc tgg    6718
Val Thr Pro Glu Ser Asn Asp Ala Glu Pro Leu Trp Ala Ile Ala Trp
1315                1320                1325                1330 cgc act aga agt gcc tcc tgg atg ctc cat cat cgg caa aca ctg gaa    6766
Arg Thr Arg Ser Ala Ser Trp Met Leu His His Arg Gln Thr Leu Glu
            1335                1340                1345 gca gcg ctg gca tagtaggcag cgaccgcgcc ataagtcgtg ggacgaagct        6818
Ala Ala Leu Ala
        1350 gcggactggg gttgcgaggt taagttcagc aagcaagggg gagacactat ggaagcttcg  6878 ttcaggccgt tcgtccgctt tatccacgaa aaacagatgc aacttctcga agagactgca  6938 aaaagtccga aaggctcctg gctgtgtgac gcgctcggtg atccggaact attcttcgcc  6998 ttgagagacg agcgtatcga cgtctactat cgcggacggg ccatctattc catcgagttc  7058 agcggtggca aggtgacacc acggaccccat gtgaagtacc tggttctcga cgaccgtgac  7118 ccttacatca agatgcagaa cgcg                                         7142
```

<210> SEQ ID NO 2
<211> LENGTH: 42
<212> TYPE: PRT
<213> ORGANISM: Rhizobium leguminosarum bv. trifolii

<400> SEQUENCE: 2

```
Met Asp Asn Lys Val Ala Lys Asn Val Glu Val Lys Lys Gly Ser Ile
1               5                   10                  15

Lys Ala Thr Phe Lys Ala Ala Val Leu Lys Ser Lys Thr Lys Val Asp
            20                  25                  30

Ile Gly Gly Ser Arg Gln Gly Cys Val Ala
        35                  40
```

<210> SEQ ID NO 3
<211> LENGTH: 373
<212> TYPE: PRT
<213> ORGANISM: Rhizobium leguminosarum bv. trifolii

<400> SEQUENCE: 3

```
Met Asp Phe Val Gln Arg Phe Val Ile Asp Arg Ser Phe His Leu Arg
1               5                   10                  15

Tyr Tyr Ser Leu Asp Ala Tyr Leu Tyr Arg Ala Val Asp Gln Val Ala
            20                  25                  30

Trp Asp Ala Asp Ile Thr His Asn Arg Leu Phe Trp Asp Ile Trp Ser
        35                  40                  45

Ala Phe Met Gln Pro Arg Ser Leu Val Asp Ala Val Glu Thr Leu Ser
    50                  55                  60

Asp Tyr Asp Pro Asp Glu Val Ala Ala Ile Glu Gly Met Cys Glu
65                  70                  75                  80

Ser Gly Ile Ile Glu Pro Val Gly Leu Lys Asp Arg Gln Phe Asp Pro
                85                  90                  95

Leu Thr Val Glu Leu Ser His Val Pro Gln Ala Trp Asp Tyr His Leu
            100                 105                 110

Val Ser Ser Arg Ile Asp Trp Ile Asn Tyr Leu Asp Gly Lys Asp Val
        115                 120                 125

Lys Arg Gln Asp Leu Glu Gln Met Asp Lys His Leu Ser Glu Glu Ala
    130                 135                 140

Val Pro Ser Asn Phe His Lys Ala Ala Asn Ser Arg Pro Lys Tyr Asp
145                 150                 155                 160
```

```
Leu Pro Ser Leu Val Pro Leu Thr Ala Phe Glu Phe Asn Asn Ser Ala
                165                 170                 175

Ser Val Ala Phe Gly His Glu Lys Ala Pro Leu Pro Asn Glu Leu Ser
            180                 185                 190

Leu Asp Ile Ile Thr Leu Leu Asn Tyr Ala Ala Lys Thr Asp
        195                 200             205

Thr Val Asn Met Tyr Ala Thr Gly Glu His Leu Arg Lys Ala Val Pro
    210                 215                 220

Ser Gly Gly Ala Arg His Pro Ile Glu Phe Tyr Val Val Gly Asp
225             230                 235                 240

Glu Ile Ala Gly Ile Glu Ala Gly Val Tyr His Tyr Asn Val Arg His
                245                 250                 255

His Arg Leu Asp Ala Ile Glu Ile Ala Ser Thr Ser Leu Lys Ala Leu
            260                 265                 270

Gln Glu Ala Ser Ser Val Leu Pro Arg Ser Arg Ser Lys Pro Phe Gly
        275                 280                 285

Phe Ala Phe Ile His Thr Cys Arg Phe Glu Arg Ser Met Phe Arg Tyr
    290                 295                 300

Arg Glu Pro Arg Ser Tyr Arg Val Met Gln Phe Asp Leu Gly His Ile
305             310                 315                 320

His Ala Asn Glu Val Leu Ala Ala Lys Ile Leu Gly Leu Asp Phe Ser
                325                 330                 335

Glu Thr Phe Ser Val Pro Glu Ser Ile Val Glu Ser Val Leu Thr Leu
            340                 345                 350

Asp Pro Phe Ile Glu Ser Ala Met Ser Ala Phe Val Val His Arg His
        355                 360                 365

Glu Asn His His Asp
    370

<210> SEQ ID NO 4
<211> LENGTH: 416
<212> TYPE: PRT
<213> ORGANISM: Rhizobium leguminosarum bv. trifolii

<400> SEQUENCE: 4

Met Ser Asp Glu Asn Gln His Gly Phe Tyr Arg Thr Ser Phe Glu Tyr
1               5                   10                  15

Ala Ser Ile Ser Trp Arg Arg Met Ile Pro Asn Val Ala Asp Thr Ile
            20                  25                  30

Val Val Thr Leu Ile Gly Ala Thr Ala Leu Gln Val Ala Ser Asn Val
        35                  40                  45

Leu Ile Thr Ile Leu Thr Leu Asn Ile Ala Phe Leu Asn Phe Cys Ser
    50                  55                  60

Leu Ile Cys Met His Asn Leu Lys Arg Gly Ala Lys Ala Asp Val Phe
65                  70                  75                  80

Ala Ala Ile Val Arg Ala Ala Cys Met Met Ile Gly Val Tyr Leu Ala
                85                  90                  95

Leu Ile Ala Val Ser Val Ala Thr Leu Glu Gly Ala Pro Arg Thr Gln
            100                 105                 110

Thr Ile Ala Phe Ile Ala Leu Ser Ala Leu Arg Pro Phe Val Ala Gly
        115                 120                 125

Trp Asn Ala Tyr Cys Ala Glu Val Phe Phe Ala Gln Gly Lys Arg Gln
    130                 135                 140

Ile Val Arg Ser Val Ile Thr Arg Ser Ser Leu Ile Tyr Ala Gly Val
```

```
                145                 150                 155                 160
Asn Leu Leu Phe Val Gly Leu Ser His Phe Ala Gly Thr Gln Asn Ser
                165                 170                 175
Ile Ile Ser Leu Leu Ile Gly Val Tyr Leu Ala Leu Phe His Asn Ala
                180                 185                 190
Leu Ala Tyr Ala Arg Ile Leu Pro Thr Glu Trp Arg Phe Ser Arg Gln
                195                 200                 205
Asp Leu Lys Asp Val Phe Ser Leu Arg Lys Leu Asp Leu Val Gly Ile
        210                 215                 220
Gly Ala Gly Leu Ser Ala Ser Phe Ile Asn Met Leu Glu Met Gly Phe
225                 230                 235                 240
Leu Ala Leu Val Gly Trp Val Ala Ala Lys Phe Pro Gln Ile Ala
                245                 250                 255
Val Phe Tyr Phe Pro Phe Phe Thr Leu Val Glu Leu Thr Ser Gly Leu
                260                 265                 270
Ala Ile Gly Leu Gly Arg Ser Val Thr Glu Arg Leu Ile Thr Pro Arg
            275                 280                 285
Pro Phe Pro Arg Leu His Val Leu Ile Ala Val Tyr Ser Thr Tyr Ser
        290                 295                 300
Leu Leu Cys Phe Leu Ile Tyr Val Gly Leu Ile Gly Val Ser Asn Arg
305                 310                 315                 320
Asp Ile Phe Ala Leu Pro Leu Ser Leu Ala Gly Leu Ala Leu Leu Phe
                325                 330                 335
Leu Ile Cys Asp Gly Leu Gln Leu Val Val Arg Gly Tyr Thr Leu Ala
            340                 345                 350
Lys Ala Asp Gly Gly Lys Leu Thr His Leu Ser Ala Ile Ala Tyr Leu
        355                 360                 365
Ala Ser Gly Val Ile Leu Ala Leu Ala Ala Val Leu Gly Ser Val Gln
        370                 375                 380
Ala Leu Ala Ile Ala Leu Val Leu Gly Pro Leu Phe Leu Ala Ile Ser
385                 390                 395                 400
Ile Pro Ala Val Gln Ser Arg Thr Ala Leu Asn Ala Leu Pro Asn Arg
                405                 410                 415

<210> SEQ ID NO 5
<211> LENGTH: 258
<212> TYPE: PRT
<213> ORGANISM: Rhizobium leguminosarum bv. trifolii

<400> SEQUENCE: 5

Met Arg Ala Ser Lys Thr Pro Ile Leu Ile Asn Gly Ser Pro Trp Leu
1               5                   10                  15
Leu Asp Phe Arg Arg Ser Ser Arg Glu Phe Asp Trp Glu Ile Ala
                20                  25                  30
Glu His Leu Glu Val Pro Glu Ala Tyr Phe Gln Ala Tyr Asp Pro Leu
            35                  40                  45
Thr Thr Trp Phe Glu Trp Phe Ser Arg Ile Gly Tyr Arg Asp Tyr Thr
        50                  55                  60
Asp Ala Glu Ala Glu Ile Glu Arg Asp Ala Glu Asn Val Arg Gln
65                  70                  75                  80
His Gln Val Ser Val Gln Pro Asp Leu Thr Leu Thr Gln Arg Leu Ser
                85                  90                  95
Ser Glu Gly Ser Ile Gln Leu Pro Val Pro Phe Leu Lys Thr Ala Asp
            100                 105                 110
```

```
Gln Phe Cys Ile Leu Ser Ser Leu Leu Tyr Ala Gly Phe Gly Val Val
        115                 120                 125

Glu Thr Arg Lys Phe His Gly Asp Thr Ile Phe Leu Lys Asn Val Pro
130                 135                 140

Ser Val Gly Ala Arg His Gly Ile Glu Ala Tyr Val Ser Leu Asp Asp
145                 150                 155                 160

Gly Arg Tyr Tyr Asp Cys Glu Gln His Arg Leu Phe Ser Ala Gly
                165                 170                 175

Tyr Arg Gly Asp Leu Arg Ser Gly Gln Ile Asp Ile Val Phe Arg Pro
            180                 185                 190

Glu Val Tyr Met Trp Arg Tyr Gln Thr Ala Ala Cys Leu Ala Asp Val
        195                 200                 205

Tyr Leu Asp Leu Gly His Ile Leu Gly Thr Leu Ser Met Val Ala Ser
210                 215                 220

Leu Tyr Asp Thr Ser Ile Thr Ser Arg Ser Ala Glu Ala Ala Pro Val
225                 230                 235                 240

Asp Leu Ile Asn Ala Val His Leu Gln Arg Ile Ala Val Asp Gly Phe
                245                 250                 255

Asn Pro

<210> SEQ ID NO 6
<211> LENGTH: 261
<212> TYPE: PRT
<213> ORGANISM: Rhizobium leguminosarum bv. trifolii

<400> SEQUENCE: 6

Met Asn Asp Glu Ile Cys Leu Thr Gly Gly Gly Arg Thr Thr Val Thr
1               5                   10                  15

Arg Arg Gly Gly Val Val Tyr Arg Glu Gly Gly Pro Trp Ser Ser Thr
                20                  25                  30

Val Ile Ser Leu Leu Arg His Leu Glu Ala Ser Gly Phe Ala Glu Ala
            35                  40                  45

Pro Ser Val Val Gly Thr Gly Phe Asp Glu Arg Gly Arg Glu Thr Leu
        50                  55                  60

Ser Phe Ile Glu Gly Glu Phe Val His Pro Gly Pro Trp Ser Glu Glu
65                  70                  75                  80

Ala Phe Pro Gln Phe Gly Met Met Leu Arg Arg Leu His Asp Ala Thr
                85                  90                  95

Ala Ser Phe Lys Pro Pro Glu Asn Ser Met Trp Arg Asp Trp Phe Gly
            100                 105                 110

Arg Asn Leu Gly Glu Gly Gln His Val Ile Gly His Cys Asp Thr Gly
        115                 120                 125

Pro Trp Asn Ile Val Cys Arg Ser Gly Leu Pro Val Gly Leu Ile Asp
130                 135                 140

Trp Glu Val Ala Gly Pro Val Arg Ala Asp Ile Glu Leu Ala Gln Ala
145                 150                 155                 160

Cys Trp Leu Asn Ala Gln Leu Tyr Asp Asp Ile Ala Glu Arg Val
                165                 170                 175

Gly Leu Gly Ser Val Thr Met Arg Ala His Gln Val Arg Leu Leu Leu
            180                 185                 190

Asp Gly Tyr Gly Leu Ser Arg Lys Gln Arg Gly Phe Val Asp Lys
        195                 200                 205

Leu Ile Thr Phe Ala Val His Asp Ala Ala Glu Gln Ala Lys Glu Ala
210                 215                 220
```

-continued

Ala Val Thr Pro Glu Ser Asn Asp Ala Glu Pro Leu Trp Ala Ile Ala
225                 230                 235                 240

Trp Arg Thr Arg Ser Ala Ser Trp Met Leu His His Arg Gln Thr Leu
        245                 250                 255

Glu Ala Ala Leu Ala
        260

<210> SEQ ID NO 7
<211> LENGTH: 7142
<212> TYPE: DNA
<213> ORGANISM: Rhizobium leguminosarum bv. trifolii
<220> FEATURE:
<221> NAME/KEY: CDS
<222> LOCATION: (1908)..(2975)
<223> OTHER INFORMATION: tfxC coding sequence
<221> NAME/KEY: CDS
<222> LOCATION: (4213)..(4968)
<223> OTHER INFORMATION: tfxE coding sequence

<400> SEQUENCE: 7

| | | | | | |
|---|---|---|---|---|---|
| cgcgtaaaag | acacgagcag | tctccgtaga | ccataagaag | cttttagagc | agccaacgca | 60 |
| tagcagccgc | ttttctaaag | ctgctagcag | cttggtgctt | attccttggt | agcgtacgat | 120 |
| tggatcgata | tacaaaagtg | taatctcgcc | actaacaaga | gccgatccga | ctcctcttac | 180 |
| tagtccggca | accttagctg | taagaaatat | tgagtgcggg | ttgtcaatcc | acatcgatac | 240 |
| gtttgctgcg | gtcttgttct | ccaaccactc | atctatttcg | gcagaatttc | cgtgatggtc | 300 |
| agccaagcaa | agttctgcga | ttgatcgccg | caatacacgg | gcgcagtcgg | cggcatctat | 360 |
| cgccgaagcg | tcaccaattt | ccgcagcgag | gttttctcgc | tgcataattt | ttttctttcc | 420 |
| tgaatcgatc | attagttgtg | ttttttgttg | ctctcgacgt | atttgcaacc | gtttgattcg | 480 |
| attgcgtatt | tgtcaaaata | ctccatatga | ttgcattttt | taaaagacaa | gataggctca | 540 |
| catttgtcag | caaatgactg | ctggcaaacc | ccaatcgcta | aatgaggtgt | tgttgcatgg | 600 |
| ataacaaggt | tgcgaagaat | gtcgaagtga | agaagggctc | catcaaggcg | accttcaagg | 660 |
| ctgctgttct | gaagtcgaag | acgaaggtcg | acatcggagg | tagccgtcag | ggctgcgtcg | 720 |
| cttaagtgaa | catccggcgg | gtgcggcaaa | cgtacccgcc | acttatgccc | tcgctttcaa | 780 |
| cgggatgttt | cgcatggact | tcgtccaacg | attcgtaatc | gaccgctctt | tccacctccg | 840 |
| ctactacagc | ctcgacgcct | atctatatcg | cgcagttgac | caggtcgcct | gggacgcaga | 900 |
| catcactcac | aatcgcctat | tttgggacat | ttggtcagca | ttcatgcagc | cgagaagtct | 960 |
| ggtagacgct | gttgagacgc | tatccgatta | cgatcccgac | gaagtggccg | cagcaatcga | 1020 |
| aggcatgtgc | gagtcgggca | tcatcgaacc | ggtgggcttg | aaagaccgcc | aatttgatcc | 1080 |
| tttgacggta | gagctgtcac | atgtgccaca | ggcatgggat | tatcacctgg | tctcaagtcg | 1140 |
| catcgactgg | atcaattatc | tggatgggaa | ggacgttaaa | cgccaggacc | ttgaacaaat | 1200 |
| ggacaagcat | ttgtcggagg | aggctgttcc | gtcgaatttt | cacaaggccg | ccaactctcg | 1260 |
| accgaaatat | gatttgccaa | gtttagtgcc | gctgacagcg | ttcgaattca | ataactcggc | 1320 |
| gtccgtcgca | ttcggtcatg | agaaggcacc | gcttccgaac | gaactgtcgc | tcgatataat | 1380 |
| cacattgctc | ctcaactatg | cggccgcaaa | gacggatacc | gtcaacatgt | atgccactgg | 1440 |
| cgagcatctg | cgaaaggccg | tcccatccgg | aggagcgcga | cacccatcg | aattctacgt | 1500 |
| ggttgtcggc | gatgagattg | caggtatcga | agctggcgta | tatcactaca | atgttcgcca | 1560 |
| tcatcggctc | gatgctatcg | aaatagcgtc | cacctcattg | aaagcactgc | aagaggcaag | 1620 |
| ctcagtgctg | ccccgatcac | ggtcaaaacc | gttcggcttt | gctttcattc | atacatgtcg | 1680 |

-continued

```
gttcgagcga agtatgtttc ggtaccgcga accgcgaagc taccgtgtga tgcagtttga    1740
tcttgggcat atccatgcca acgaggtttt ggctgccaaa atcctcggcc tcgatttcag    1800
tgaaaccttt tctgtgccgg aaagcatagt tgagagcgtc ttgacgctcg atccgttcat    1860
cgagtccgcg atgtcagcct tgtcgtcca cagacacgag aaccacc atg att gaa       1916
                                                  Met Ile Glu
                                                   1
```

```
ctg cgc ccg ctt ctc caa ctg aat ctt gaa gat gga atc ccg gtc ctc      1964
Leu Arg Pro Leu Leu Gln Leu Asn Leu Glu Asp Gly Ile Pro Val Leu
    5                   10                  15 aaa gac ctc ctg acc gcc gac agc ttt tcc ttc acc gat gtt gaa ctc      2012
Lys Asp Leu Leu Thr Ala Asp Ser Phe Ser Phe Thr Asp Val Glu Leu
 20                  25                  30                  35 ttg cgg tac att cca gcc att gcc aag aac acc ccc gcc cag act cgg      2060
Leu Arg Tyr Ile Pro Ala Ile Ala Lys Asn Thr Pro Ala Gln Thr Arg
                40                  45                  50 gat ttg gct gcc tct gtt gct gat gcg ctg gat gtt gac caa acc acc      2108
Asp Leu Ala Ala Ser Val Ala Asp Ala Leu Asp Val Asp Gln Thr Thr
             55                  60                  65 gcg ctc gca gcc atc gaa gca ttg gtt gag ctt ggt ctt ttg gtg cca      2156
Ala Leu Ala Ala Ile Glu Ala Leu Val Glu Leu Gly Leu Leu Val Pro
         70                  75                  80 tcc gcg tcg atc tcc tcg cag aag gca ggg atc cag ttg tgg gtg gat      2204
Ser Ala Ser Ile Ser Ser Gln Lys Ala Gly Ile Gln Leu Trp Val Asp
 85                  90                  95 aag gga tgg gtg gac gca ctg atc ctg cat ttc gcg agc aga aat ctc      2252
Lys Gly Trp Val Asp Ala Leu Ile Leu His Phe Ala Ser Arg Asn Leu
100                 105                 110                 115 aat tat aat gac gat cca att gaa ttt ggc ggg ttg gag gat atc aaa      2300
Asn Tyr Asn Asp Asp Pro Ile Glu Phe Gly Gly Leu Glu Asp Ile Lys
                120                 125                 130 agc tat ccc gaa ccg atg gaa tcg aag cgt agg aaa cgc ggc acc gcc      2348
Ser Tyr Pro Glu Pro Met Glu Ser Lys Arg Arg Lys Arg Gly Thr Ala
            135                 140                 145 acg cga ttg gtc aag ccg tcc cgg gag ctg gca gct gca gtc ata ctg      2396
Thr Arg Leu Val Lys Pro Ser Arg Glu Leu Ala Ala Ala Val Ile Leu
        150                 155                 160 gac ggg ctc atg aac agg cgc tcg ttc aaa ccc ttc aca cgc aaa caa      2444
Asp Gly Leu Met Asn Arg Arg Ser Phe Lys Pro Phe Thr Arg Lys Gln
165                 170                 175 ctg tcg atc acc gag gtc agc gag ata ctt tgg ttt ggg aac ctc tat      2492
Leu Ser Ile Thr Glu Val Ser Glu Ile Leu Trp Phe Gly Asn Leu Tyr
180                 185                 190                 195 gcg cga gaa cgc gcg gtc atc gct gaa aat cgt gac ttc gag tct cct      2540
Ala Arg Glu Arg Ala Val Ile Ala Glu Asn Arg Asp Phe Glu Ser Pro
                200                 205                 210 cgc gat ata gct ttc gac agc gcc ttc tca gcg ttg tcc acc ttt gtt      2588
Arg Asp Ile Ala Phe Asp Ser Ala Phe Ser Ala Leu Ser Thr Phe Val
            215                 220                 225 gtc aca tat gga cag atc gat tgg cag gat ggc tcg ttg cca ccc gga      2636
Val Thr Tyr Gly Gln Ile Asp Trp Gln Asp Gly Ser Leu Pro Pro Gly
        230                 235                 240 gtc tat cgt tac aat gtc gtc aat cac gaa ctt gaa gca atc aga gcc      2684
Val Tyr Arg Tyr Asn Val Val Asn His Glu Leu Glu Ala Ile Arg Ala
245                 250                 255 ggt gat ttc aag ctg gac atg gca aaa ctc gct atc ggt cag agt cgg      2732
Gly Asp Phe Lys Leu Asp Met Ala Lys Leu Ala Ile Gly Gln Ser Arg
260                 265                 270                 275
```

```
                                                        -continued gct tcg agc ggg cta ttc acg ttt gtg atc tgc ggc gat ttg aag tca    2780
Ala Ser Ser Gly Leu Phe Thr Phe Val Ile Cys Gly Asp Leu Lys Ser
            280                 285                 290 tac aca tcg cgg tac agg cac gag cgg agc tac cgc aat ctg ctg atc    2828
Tyr Thr Ser Arg Tyr Arg His Glu Arg Ser Tyr Arg Asn Leu Leu Ile
            295                 300                 305 aac acc tca cag ctc gcc caa ttc tat ttg acc ctc gca acg atc aac    2876
Asn Thr Ser Gln Leu Ala Gln Phe Tyr Leu Thr Leu Ala Thr Ile Asn
            310                 315                 320 gac ttc aac acc ttt ctc acg ccc gcc atc cac gat gag aaa atg cat    2924
Asp Phe Asn Thr Phe Leu Thr Pro Ala Ile His Asp Glu Lys Met His
325                 330                 335 ctg ttt ctt gaa gcg gag gac gac ctc ccg ctt tat ctc gtc acg gca    2972
Leu Phe Leu Glu Ala Glu Asp Asp Leu Pro Leu Tyr Leu Val Thr Ala
340                 345                 350                 355 ggc tagagcatga gcgacgaaaa ccagcatggg ttctatcgga cttcgttcga         3025
Gly atacgcatcg atcagttggc ggagaatgat tcccaatgtg gctgacacta tcgtcgtcac  3085
gctcatcggc gctactgcac ttcaggtggc gtcaaatgtt ctgatcacga tactgaccct  3145
caatatcgct tttctgaact tttgctcgct tatctgcatg cacaatctga aaagagggc   3205 aaaggccgac gtatttgctg caatcgtccg cgctgcttgc atgatgatcg gggtctacct  3265
ggcgcttatc gcggtctccg tcgccaccct cgaaggtgca ccgcgtaccc aaaccattgc  3325
tttcatagca ctgtctgcgc tccggccgtt tgtggctgga tggaatgctt actgtgcgga  3385
ggtttttttc gcccagggaa aacgacaaat tgtgcgaagc gtcatcacga gatcgtcgct  3445
gatctatgca ggagttaatc tgctctttgt cgggctgtcg catttcgctg cactcaaaa   3505 ttcgatcata tcgcttctca tcggcgtata tcttgctctc ttccacaacg ccctggccta  3565
cgccagaatc ctgccgaccg aatggaggtt cagtcgccag gatttgaagg atgtcttctc  3625
acttcggaag cttgatctgg tcggaatcgg ggcagggctt tctgcgtctt ttatcaacat  3685
gctcgaaatg gggtttcttg cattagttgg gtgggtggtg gcagcaaagt ttccgcaaat  3745
cgcggttttt tatttcccgt ttttcacttt ggtggaattg acgagcggac ttgcgattgg  3805
gcttggacgc tcagtcaccg aacgtttgat tacgccgcgc ccgtttcccc ggctgcacgt  3865
cttgatcgcc gttacagca cgtattcgtt gctctgcttc ttgatctacg ttggattaat   3925
aggtgtgagc aatcgggaca tatttgctct cccgctgtcg cttgccggat ggcgctact   3985 tttcctgatc tgcgacgggc tgcagcttgt ggttcgggga tatacgctcg ccaaagctga  4045
cggaggcaag ctcacgcatc tcagcgccat tgcatacctc gcctctggag tgatcctcgc  4105
gctggcggcc gtcttgggct cggttcaagc gttggccatc gctttggtct tgggaccgct  4165
gttccttgca atctccattc ccgccgttca aagtcgaact gccctaa atg cac tac    4221
                                                    Met His Tyr cga aca gat aaa ccg aaa gta ttc gta acc gac tcc ggc agg ttt gtt    4269
Arg Thr Asp Lys Pro Lys Val Phe Val Thr Asp Ser Gly Arg Phe Val
360                 365                 370                 375 gct gac tgc cag ata att ctg ctt ggt cgc aag atc ata tgt acg gga    4317
Ala Asp Cys Gln Ile Ile Leu Leu Gly Arg Lys Ile Ile Cys Thr Gly
            380                 385                 390 acc gat ctt cag tac gag att gcg gtt gca aaa gca aag tct gag ctt    4365
Thr Asp Leu Gln Tyr Glu Ile Ala Val Ala Lys Ala Lys Ser Glu Leu
            395                 400                 405 gcg gag agg atc gcg ttt gca tca cca gac gcc ttc aat gcg cga gtg    4413
Ala Glu Arg Ile Ala Phe Ala Ser Pro Asp Ala Phe Asn Ala Arg Val
            410                 415                 420
```

-continued

| | |
|---|---|
| acg cgg gtt gca agg cgt ctc atg ctc gaa gct acc aat gcc ttc aac<br>Thr Arg Val Ala Arg Arg Leu Met Leu Glu Ala Thr Asn Ala Phe Asn<br>425                             430                              435 | 4461 |
| aga gaa tcc gtc acc ctg ccg ttg agc ttg ttc gta acg cgg cca cat<br>Arg Glu Ser Val Thr Leu Pro Leu Ser Leu Phe Val Thr Arg Pro His<br>440                             445                          450                        455 | 4509 |
| ctg tgc tgg atg cgc ggc aac aac tcc aca gga ttt gcc gca cat ccc<br>Leu Cys Trp Met Arg Gly Asn Asn Ser Thr Gly Phe Ala Ala His Pro<br>                        460                          465                          470 | 4557 |
| cgg cgc aag gca gca att gaa cac gcg gtc aat gag gtt tta gag cgc<br>Arg Arg Lys Ala Ala Ile Glu His Ala Val Asn Glu Val Leu Glu Arg<br>               475                          480                          485 | 4605 |
| ggc tgg aac gct cgg ttt cga cga gat cag cag tct ctt ctt aag ttg<br>Gly Trp Asn Ala Arg Phe Arg Arg Asp Gln Gln Ser Leu Leu Lys Leu<br>               490                          495                          500 | 4653 |
| gcc acg atc cga cga gac ggt tca aca gct tgg gta cac gaa tcg agg<br>Ala Thr Ile Arg Arg Asp Gly Ser Thr Ala Trp Val His Glu Ser Arg<br>505                             510                              515 | 4701 |
| ctc cgc cag gtt tcc tac tgc ttg gcc aac gcc cgt gtt gcg gga cat<br>Leu Arg Gln Val Ser Tyr Cys Leu Ala Asn Ala Arg Val Ala Gly His<br>520                           525                          530                        535 | 4749 |
| gtc ggt tgg ggt tcc gca gtt cgc aga acg acc gaa gcg gca gtg gaa<br>Val Gly Trp Gly Ser Ala Val Arg Arg Thr Thr Glu Ala Ala Val Glu<br>               540                          545                          550 | 4797 |
| gct gca act agt gaa gcc cat gcg atg agt gcg tcg ggg cag gat tac<br>Ala Ala Thr Ser Glu Ala His Ala Met Ser Ala Ser Gly Gln Asp Tyr<br>               555                          560                          565 | 4845 |
| ggt cgc ggc gga acc ggc gtg tcg gag ctt ccc tcg caa cac gac caa<br>Gly Arg Gly Gly Thr Gly Val Ser Glu Leu Pro Ser Gln His Asp Gln<br>570                             575                              580 | 4893 |
| atc gcg ttt gtc gag agg cag ccg gtg cgc atc gat gac gtc act cat<br>Ile Ala Phe Val Glu Arg Gln Pro Val Arg Ile Asp Asp Val Thr His<br>585                             590                          595 | 4941 |
| tac gtg ata cag gcg gtg agt tat tca tgagagcaag caaaacaccg<br>Tyr Val Ile Gln Ala Val Ser Tyr Ser<br>600                           605 | 4988 |
| atcttgataa acggctctcc gtggttgtta gatttccgtc ggcggtcaag ccgagaattc | 5048 |
| gattgggaaa ttgccgaaca tctagaggtg cccgaagcat attttcaggc gtatgacccg | 5108 |
| ctaacaactt ggttcgagtg gttttctcgg atcggctatc gagattacac cgatgctgag | 5168 |
| gccgaaattg agcgagatgc cgaggaaaat gtacggcagc accaagtttc cgttcaaccc | 5228 |
| gatctcacgc tgacccagcg cctatcgagc gaaggctcga tccagcttcc agttccgttc | 5288 |
| ctaaaaacgg ccgatcaatt ttgtatcttg tcgtcgctcc tgtacgccgg ttttggagtg | 5348 |
| gttgagacgc ggaaattcca cggtgacacg atcttcctaa aaaacgtacc ttcggttgga | 5408 |
| gcgcgtcacg gcattgaggc ttatgttttcc ctggatgacg ggcgctatta ttacgactgt | 5468 |
| gagcagcatc ggttgttttc cgcaggctat cggggtgatc tacggagcgg tcagatcgat | 5528 |
| atcgtatttc ggcctgaggt atacatgtgg cgttatcaaa ccgctgcctg tcttgccgat | 5588 |
| gtctacctcg accttggcca catattaggt actctatcga tggtggcgtc cctctatgac | 5648 |
| acgtctatca cgagccgctc tgcagaagcc gctcctgtag acttgatcaa tgcggtgcat | 5708 |
| ctccagcgaa tagccgttga tggatttaat ccataggcgc aggacgggaa tgcctgcgaa | 5768 |
| ctgaagaagg ccgacgatcc gttttttctct tgatgaacgc cgtcggccag tcgtccgttt | 5828 |
| tgggccgtaa gcgctgaccc agcggcggca acagcgaccg tgtctttatg gcggcttgcc | 5888 |

-continued

```
aacgacagga gcgaggccct tgaggtgcag aaatcgttgc cgggggggcga aggctgaaag      5948 gtaaacgcgc cgcttgtggt gctactaatg gaatccaggt gggtgccatg aatgatgaga      6008
tttgcctgac aggtggcgga cgaacgactg tcacgcggcg cggcggagtc gtgtatcgcg      6068
aaggcggccc gtggtcatca accgtcattt cgctcctgcg gcatctggaa gcctctggct      6128
tcgctgaagc tccttccgtt gtcggcaccg gtttcgatga gcgcggccgg gagacattat      6188
cgtttatcga gggtgagttt gttcacccag gcccttggtc ggaggaggct tttccgcaat      6248
ttggaatgat gttgcggcga ctgcacgatg ccaccgcctc gttcaaacct cccgaaaact      6308
cgatgtggcg cgattggttc gggcgtaacc tcggtgaggg tcaacacgta ataggacact      6368
gcgacacagg cccatggaac attgtttgcc ggtcaggatt gcctgtcggg ttgatagatt      6428
gggaggtggc tgggcctgtc agggcggata tcgaattggc ccaggcttgt tggctgaatg      6488
cccagctcta cgatgacgac attgcggaga gggtcggatt aggctctgtg accatgagag      6548
cgcatcaagt tcgcctgctg cttgacggct atggtctgtc tcggaagcaa cgcggcggct      6608
tcgtcgacaa gctaatcacg ttcgcagttc acgatgcggc cgagcaggcg aaagaggcgg      6668
ctgtcacgcc agagtcgaac gatgcggaac cgctatgggc aattgcctgg cgcactagaa      6728
gtgcctcctg gatgctccat catcggcaaa cactggaagc agcgctggca tagtaggcag      6788
cgaccgcgcc ataagtcgtg ggacgaagct gcggactggg gttgcgaggt taagttcagc      6848
aagcaagggg gagacactat ggaagcttcg ttcaggccgt tcgtccgctt tatccacgaa      6908
aaacagatgc aacttctcga agagactgca aaaagtccga aaggcctg gctgtgtgac        6968 gcgctcggtg atccggaact attcttcgcc ttgagagacg agcgtatcga cgtctactat      7028
cgcggacggg ccatctattc catcgagttc agcggtggca aggtgacacc acggacccat      7088
gtgaagtacc tggttctcga cgaccgtgac ccttacatca agatgcagaa cgcg            7142
```

<210> SEQ ID NO 8
<211> LENGTH: 356
<212> TYPE: PRT
<213> ORGANISM: Rhizobium leguminosarum bv. trifolii

<400> SEQUENCE: 8

```
Met Ile Glu Leu Arg Pro Leu Gln Leu Asn Leu Glu Asp Gly Ile
  1               5                  10                  15

Pro Val Leu Lys Asp Leu Leu Thr Ala Asp Ser Phe Ser Phe Thr Asp
                 20                  25                  30

Val Glu Leu Leu Arg Tyr Ile Pro Ala Ile Ala Lys Asn Thr Pro Ala
             35                  40                  45

Gln Thr Arg Asp Leu Ala Ala Ser Val Ala Asp Ala Leu Asp Val Asp
         50                  55                  60

Gln Thr Thr Ala Leu Ala Ala Ile Glu Ala Leu Val Glu Leu Gly Leu
 65                  70                  75                  80

Leu Val Pro Ser Ala Ser Ile Ser Ser Gln Lys Ala Gly Ile Gln Leu
                     85                  90                  95

Trp Val Asp Lys Gly Trp Val Asp Ala Leu Ile Leu His Phe Ala Ser
                100                 105                 110

Arg Asn Leu Asn Tyr Asn Asp Asp Pro Ile Glu Phe Gly Gly Leu Glu
            115                 120                 125

Asp Ile Lys Ser Tyr Pro Glu Pro Met Glu Ser Lys Arg Arg Lys Arg
        130                 135                 140

Gly Thr Ala Thr Arg Leu Val Lys Pro Ser Arg Glu Leu Ala Ala Ala
145                 150                 155                 160
```

```
Val Ile Leu Asp Gly Leu Met Asn Arg Ser Phe Lys Pro Phe Thr
                165                 170                 175

Arg Lys Gln Leu Ser Ile Thr Glu Val Ser Glu Ile Leu Trp Phe Gly
        180                 185                 190

Asn Leu Tyr Ala Arg Glu Arg Ala Val Ile Ala Glu Asn Arg Asp Phe
        195                 200                 205

Glu Ser Pro Arg Asp Ile Ala Phe Asp Ser Ala Phe Ser Ala Leu Ser
        210                 215                 220

Thr Phe Val Val Thr Tyr Gly Gln Ile Asp Trp Gln Asp Gly Ser Leu
225                 230                 235                 240

Pro Pro Gly Val Tyr Arg Tyr Asn Val Asn His Glu Leu Glu Ala
                245                 250                 255

Ile Arg Ala Gly Asp Phe Lys Leu Asp Met Ala Lys Leu Ala Ile Gly
                260                 265                 270

Gln Ser Arg Ala Ser Ser Gly Leu Phe Thr Phe Val Ile Cys Gly Asp
                275                 280                 285

Leu Lys Ser Tyr Thr Ser Arg Tyr Arg His Glu Arg Ser Tyr Arg Asn
        290                 295                 300

Leu Leu Ile Asn Thr Ser Gln Leu Ala Gln Phe Tyr Leu Thr Leu Ala
305                 310                 315                 320

Thr Ile Asn Asp Phe Asn Thr Phe Leu Thr Pro Ala Ile His Asp Glu
                325                 330                 335

Lys Met His Leu Phe Leu Glu Ala Glu Asp Asp Leu Pro Leu Tyr Leu
                340                 345                 350

Val Thr Ala Gly
        355

<210> SEQ ID NO 9
<211> LENGTH: 252
<212> TYPE: PRT
<213> ORGANISM: Rhizobium leguminosarum bv. trifolii

<400> SEQUENCE: 9

Met His Tyr Arg Thr Asp Lys Pro Lys Val Phe Val Thr Asp Ser Gly
1               5                   10                  15

Arg Phe Val Ala Asp Cys Gln Ile Ile Leu Leu Gly Arg Lys Ile Ile
                20                  25                  30

Cys Thr Gly Thr Asp Leu Gln Tyr Glu Ile Ala Val Ala Lys Ala Lys
            35                  40                  45

Ser Glu Leu Ala Glu Arg Ile Ala Phe Ala Ser Pro Asp Ala Phe Asn
        50                  55                  60

Ala Arg Val Thr Arg Val Ala Arg Leu Met Leu Glu Ala Thr Asn
65                  70                  75                  80

Ala Phe Asn Arg Glu Ser Val Thr Leu Pro Leu Ser Leu Phe Val Thr
                85                  90                  95

Arg Pro His Leu Cys Trp Met Arg Gly Asn Asn Ser Thr Gly Phe Ala
                100                 105                 110

Ala His Pro Arg Arg Lys Ala Ala Ile Glu His Ala Val Asn Glu Val
            115                 120                 125

Leu Glu Arg Gly Trp Asn Ala Arg Phe Arg Arg Asp Gln Gln Ser Leu
        130                 135                 140

Leu Lys Leu Ala Thr Ile Arg Arg Asp Gly Ser Thr Ala Trp Val His
145                 150                 155                 160

Glu Ser Arg Leu Arg Gln Val Ser Tyr Cys Leu Ala Asn Ala Arg Val
```

-continued

```
                165                 170                 175

Ala Gly His Val Gly Trp Gly Ser Ala Val Arg Arg Thr Thr Glu Ala
            180                 185                 190

Ala Val Glu Ala Ala Thr Ser Glu Ala His Ala Met Ser Ala Ser Gly
        195                 200                 205

Gln Asp Tyr Gly Arg Gly Gly Thr Gly Val Ser Glu Leu Pro Ser Gln
    210                 215                 220

His Asp Gln Ile Ala Phe Val Glu Arg Gln Pro Val Arg Ile Asp Asp
225                 230                 235                 240

Val Thr His Tyr Val Ile Gln Ala Val Ser Tyr Ser
            245                 250
```

BIOLOGICAL CONTROL OF CROWN GALL DISEASE

CROSS-REFERENCE TO RELATED APPLICATIONS

This application claims the benefit of U.S. Provisional Ser. Application No. 60/224,929 filed Aug. 11, 2000.

STATEMENT REGARDING FEDERALLY SPONSORED RESEARCH OR DEVELOPMENT

This invention was made with United States Government support awarded by the United States Department of Agriculture under grant number USDA 00-CRHF-0-6055. The United States has certain rights in this invention.

BACKGROUND OF THE INVENTION

A genus of plant pathogenic bacteria is the genus Agrobacteria. *Agrobacterium* bacteria are naturally occurring plant genetic engineers. Members of the *Agrobacterium* genus natively have the ability to transfer a segment of DNA from a plasmid hosted by the bacterium into the genome of a cell of a living plant. The DNA transferred into the plant (the T-DNA) causes the plant cells to initiate two activities. One activity is to manufacture a class of chemicals, called opines, which can be metabolized by the bacteria as a food source. The other activity is to initiate the growth of a tumorous mass referred to as a crown gall.

*Agrobacterium* initiates crown gall growth in order to create a microenvironment, the crown gall, where the bacteria can thrive and multiply. Unfortunately, the crown gall itself saps metabolic energy from the plant that would otherwise be directed at producing vegetative growth or fruit, thus reducing the yield that would otherwise be produced by that plant. In some perennial plant species where the plant is long-lived, such as grapes, stonefruits and roses, the impact of crown gall disease can be significant. For example, strains of the bacteria *Agrobacterium vitis*, which attacks vines, are the primary cause of grapevine crown gall, which is the most economically damaging bacterial disease of grape worldwide.

A number of different approaches exist for controlling plant diseases in commercial agriculture. One approach is based upon the application to plants or soil of chemical agents toxic or inimical to the disease-causing organism. A second approach is based on the development of plant varieties that are resistant to infection by the particular disease or strain of disease. One other approach is based on the use of a biological organism to control the disease-causing organism. This latter strategy is referred to as biocontrol.

Biocontrol agents control plant disease by secreting chemicals that act to inhibit or kill the disease-causing organism, or by simply occupying the ecological niche that would otherwise be available to the disease-causing organism. Some microorganisms are capable of inhibiting the growth of competing microbial strains through the use of toxins. If a bacterium can emit a broad-spectrum antibacterial toxin into its local environment, then that bacterium will have less competition in its ecological niche. As a result, many bacteria, and other microorganisms, have evolved genes for toxins. Often the plasmids that carry the genes encoding these toxins also carry genes conferring on its host immunity to that particular toxin. This is advantageous since obviously the toxin-secreting organism must have some mechanism to avoid the toxicity of its own toxin if the organism is to successfully populate the ecological niche it has cleared for itself.

Effective strategies to control crown gall by using biocontrol agents to control *Agrobacterium* growth are now known to exist. One problem associated with combating crown gall disease, however, is that different *Agrobacterium* species normally inhabit and attack plants in differing ecological micro-zones of the plant, as well as different plant species. For example, *Agrobacterium rhizogenes* normally lives in the root environment (the rhizosphere) of plants and attacks plant roots, while *Agrobacterium tumefaciens* normally attacks and infects plant stems or crowns. As a result, biocontrol strategies for crown gall disease must be focused on the micro-environment of the particular plant species and strains of *Agrobacterium* sought to be suppressed.

*Agrobacterium rhizogenes* strain K84, for example, is the most studied crown gall biological control strain and is commercially utilized for disease control on stone fruits worldwide. Strain K84 biological control is thought to be primarily due to the production of two plasmid-encoded antibiotics, agrocins 84 and 434, encoded by genes on pAgK84 and pAgK434 respectively, each of which accounts for a portion of the observed disease control. Agrocin 84, an adenine analog, is effective against tumorigenic strains carrying nopaline/agrocinopine pTi plasmids, and requires the accC gene in the target strain for activity. Agrocin 434, a di-substituted cytidine analog, is effective against, and specific for, a broad range of *A. rhizogenes* strains. The commercial application of the K84 biological control system, however, is limited to stone fruits as pathogenic *Agrobacterium* strains of other crops are not inhibited by K84.

With respect to the *Agrobacterium vitis* strains, the causative agents of grapevine crown gall, no effective preventative control measures are commercially available. One prior attempt to use a biocontrol technique to combat crown gall in grape was based on the *Agrobacterium vitis* bacterial strain F2/5. Strain F2/5 is a non-tumorigenic *Agrobacterium* strain which may be applied to grapevines to occupy the ecological niches that might otherwise be occupied by tumorigenic strains. This strategy has met with some success, but the success is both grape-specific, i.e. does not work on other plant species, and is variable depending on the identity of the virulent *A. vitis* strain causing the disease. For example, F2/5 is ineffective on non-grapevine host plants, such as *Nicotiana glauca*, sunflower or tomato, and ineffective against various pathogenic *A. vitis* strains, such as CG78, as well as other *A. tumefaciens* biovars.

What is needed is a biocontrol agent with a broader target range to help control crown gall disease and, in particular, crown gall disease in grape plants.

BRIEF SUMMARY OF THE INVENTION

The present invention is summarized as a method for controlling crown gall disease in plants using an effective quantity of α-proteobacteria strain that produces trifolitoxin (TFX). The α-proteobacteria strain may be a biologically pure culture of an isolated TFX producing α-proteobacteria strain, as well as an α-proteobacteria strain genetically engineered to produce TFX. The present invention also includes the biocontrol agent of the above method, and a plant treated with the biological control agent.

The biocontrol agent is characterized as an α-proteobacteria strain genetically engineered to produce trifolitoxin (TFX). The α-proteobacteria strain employed may include any one of the many strains of *Agrobacterium*, including

*Agrobacterium vitis* and, in particular, *A. vitis* F2/5. The α-proteobacteria strain employed may be genetically engineered to produce TFX by introducing a genetic construct into the *Agrobacterium* so as to cause the *Agrobacterium* to carry and express the tfx operon from *Rhizobium*. The bacterium may also be genetically engineered to produce TFX by introducing a pT2TFXK plasmid into the *Agrobacterium*. The biocontrol agent may also be the strain *Agrobacterium vitis* F2/5 (pT2TFXK), ATCC Patent Deposit Designation PTA-2356.

It is an object of the present invention to create a biocontrol agent effective in inhibiting the occurrence of crown gall disease on plants and, in particular, in vine crop plant species.

It is a feature of the present invention that a novel and effective method to inhibit crown gall disease cause by many strains is made possible for the first time.

It is another feature of the present invention that a novel and effective method to inhibit crown gall disease above ground in vine crop plant species is now made possible.

Other object advantages and features of the present invention will become apparent from the following description and drawings.

DETAILED DESCRIPTION OF THE INVENTION

The present invention provides a method for controlling crown gall disease in plants using an effective quantity of an α-proteobacteria strain that produces trifolitoxin (TFX). The α-proteobacteria strain may be a biologically pure culture of an isolated TFX producing α-proteobacteria strain, as well as an α-proteobacteria strain genetically engineered to produce TFX. The present invention also includes the biocontrol agent of the above method, and a plant treated with the biological control agent.

Figure 2:
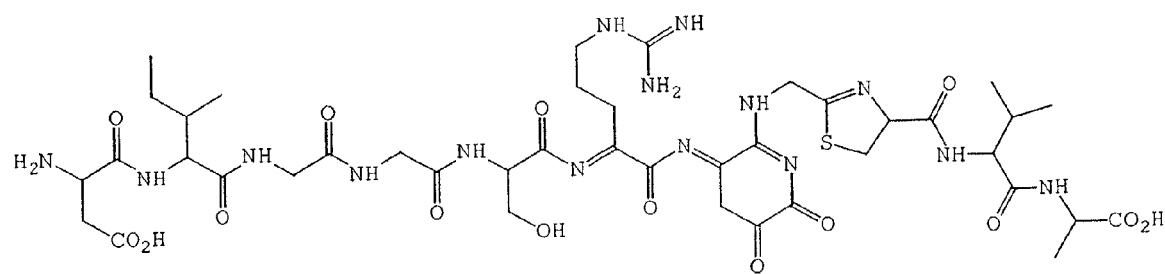
FIG. 2 illustrates the putative chemical structure of the trifolitoxin peptide.

Trifolitoxin is a peptide antibiotic natively produced by *Rhizobium leguminosarum* bv. *trifolii* T24, which natively inhabits the rhizosphere of bean plants. Antibiotic production and resistance functions are encoded by a seven-gene tfx operon and an unlinked tfuA gene. Breil et al., "DNA sequence and mutational analysis of genes involved in the production and resistance of the antibiotic peptide trifolitoxin", *J. Bacteriol.* 175(12):3693–3702 (1993); and Breil et al., "A newly discovered gene, tfuA, involved in the production of the ribosomally synthesized peptide antibiotic trifolitoxin", *J. Bacteriol.* 178(14):4150–4156 (1996), incorporated herein by reference. TFX is derived from post-translational cleavage and modification of the tfxA gene product, and effectively inhibits growth of members of the α-proteobacteria, including strains of *Ochrobactrum*, *Rhodobacter, Rhodospeudomonas, Brucella*, and *Rhizobium*. TFX is highly specific for this group, as previously demonstrated by a lack of observable effect on non-Rhizobiaceae bacteria in the bean rhizosphere. Robleto et al., "Effects of bacterial antibiotic production on rhizosphere microbial communities from a culture-independent perspective", *Appl. Environ. Microbiol* 74:5020–5022 (1998). A putative structure of active TFX is set forth in FIG. 2.

We have discovered that it is possible to transfer a genetic construct encoding the production of TFX, and resistance to it, into an α-proteobacteria strain, such as *Agrobacterium*, and that such engineered bacteria can function as effective biocontrol agents for crown gall disease in plants. We have also discovered that TFX is inhibitory against a wide range of *Agrobacterium vitis* strains, including several strains that are poorly controlled by the strain, *A. vitis* F2/5. In addition, TFX production, expressed from the stable plasmid pT2TFXK, enhances the biological control activity of *A. vitis* F2/5 by making it both effective against strains that are not normally controlled by *A. vitis* F2/5, and by broadening its effective host plant range.

The biocontrol agent of the present invention is generally defined to include an α-proteobacteria strain that produces TFX. In one embodiment the biocontrol agent is an α-proteobacteria strain which has been genetically modified to produce TFX. Strains of α-proteobacteria are well known in the art. Suitable strains of α-proteobacteria are also described in Triplett et al., "Expression of tfx and Sensitivity to the Rhizobial Peptide Antibiotic Trifolitoxin in a Taxonomically Distinct Group of α-Proteobacteria Including the Animal Pathogen *Brucella abortus*", *App. Environ. Microbiol.*, 60(11):4163–4166 (1994), which is incorporated herein by reference. *Agrobacterium* is one selection of α-proteobacteria which have shown effectiveness in serving as biocontrol agents in accordance with the present invention. An example of one effective *Agrobacterium* species is *Agrobacterium vitis* and, in particular, the *A. vitis* strain F2/5.

Figure 1:
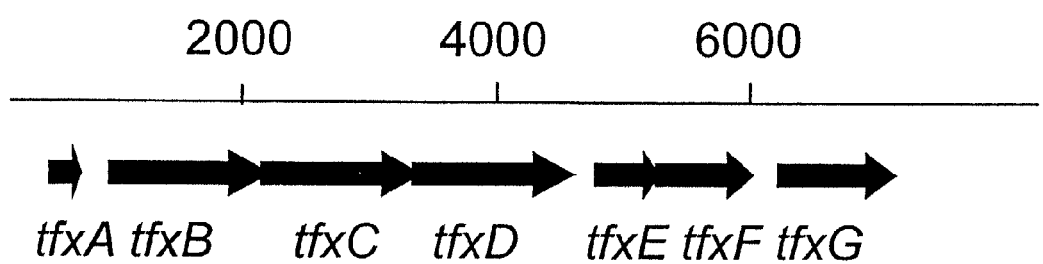
FIG. 1 is an illustration of the structure of the tfx operon.

The α-proteobacteria employed may be genetically engineered to produce TFX by introducing a nucleotide sequence into the bacteria that causes the bacteria to carry and express the tfx operon. The structure of the tfx operon is illustrated in FIG. 1. The operon includes seven genes designated tfxA through tfxG. The sequence for the tfx operon from *Rhizobium leguminosarum* bv. *Trifolii* is set forth in SEQ ID NO:1. The tfxA gene spans niycleotide bases 597 to 725, and its deduced amino acid sequence is set forth in SEQ ID NO:2. The tfxB gene spans nucleotide bases 794 to 1915, and its deduced amino acid sequence is set forth in SEQ ID NO:3. The tfxC gene spans nucleotide bases 1908 to 2978, and its deduced amino acid sequence is set forth in SEQ ID NO:8. The tfxD gene spans nucleotide bases 2982 to 4232, and its deduced amino acid sequence is set forth in SEQ ID NO:4. The tfxE gene spans nucleotide bases 4213 to 4971, and its deduced amino acid sequence is set forth in SEQ ID NO:9. The tfxF gene spans nucleotide bases 4968 to 5744, and its deduced amino acid sequence is set forth in SEQ ID NO:5. The tfxG gene spans nucleotide bases 5996 to 6781, and its deduced amino acid sequence is set forth in SEQ ID NO:6.

It is well known that copies of genes vary from strain to strain within a species. Such variations are referred to here as allelic variations. Accordingly, there are likely to be tfx operons in other bacterial species which may or may not have a sequence identical to SEQ ID NO:1 at each nucleotide. Such allelic variations to SEQ ID NO:1, as may exist, would not compromise the ability of the operon to effectively produce TFX in exactly the same manner as SEQ ID NO:1, and thus may be used in the practice of the present invention.

Many methods for introducing genetic constructs into bacteria so as to cause the bacteria to carry and express specific genes of interest are commonly known in the art, and may be employed in the present invention. For example, one may consider introducing a genetic construct containing the tfx operon into a bacterium so as to integrate at least one copy of the tfx operon into the bacterium's genome. Alternatively, one may consider introducing into a bacterium a plasmid that carries and expresses the tfx operon. In the latter case, the plasmid employed may include, with limitation, the pT2TFXK plasmid described in Triplett et al., "Expression of tfx and Sensitivity to the Rhizobial Peptide Antibiotic Trifolitoxin in a Taxonomically Distinct Group of α-Proteobacteria Including the Animal Pathogen *Brucella abortus*", *App. Environ. Microbiol.*, 60(11):4163–4166 (1994), which is incorporated herein by reference. Although plasmid-borne traits are frequently unstable, pT2TFXK contains the RK2 plasmid-partitioning locus that confers a high degree of stability both in vitro and under field conditions. Stability of TFX expression would be beneficial when the biocontrol agent is inoculated onto the plant only at planting time, such as when roots are dipped in a bacterial suspension prior to planting.

In one embodiment, the biocontrol agent is the strain *Agrobacterium vitis* F2/5 (pT2TFXK) deposited with the American Type Culture Collection on Aug. 8, 2000, and provided Patent Deposit Designation PTA-2356. Several features of F2/5(pT2TFXK) suggest that it is a safe agent for crown gall biological control. First, because of TFX's narrow range of toxicity, bacterial TFX production has little effect on non-target organisms. In addition, *A. vitis* itself is host-plant-specific, and has only been isolated from the grape rhizosphere, vineyard soils, and infested grapevines. Also, *A. vitis* survives poorly in bulk soil and non-grape rhizospheres, suggesting that F2/5(pT2TFXK) applied to grapevines would be unlikely to escape the vineyard or to affect the rhizospheres of other vineyard plants. This is in contrast to the commercially utilized *A. radiobacter* K84 strain, which has been shown to spread through fallow soil and to colonize the rhizosphere of many plant species. Further, pT2TFXK lacks tra genes and is therefore not self-mobilizable. A derivative of *A. radiobacter* K84, K1026, carries a Δtra derivative of the self-transmissible pAgK84 is being used in Australia for control of crown gall.

The method of the present invention is generally defined to include the step of introducing onto a plant an amount of the TFX-producing α-proteobacteria strain which effectively inhibits or reduces crown gall growth as compared to a plant not treated with the TFX-producing α-proteobacteria. The TFX-producing α-proteobacteria strain may be an α-proteobacteria strain genetically engineered to produce TFX as described above, or a substantially pure culture of an α-proteobacteria strain that naturally produces TFX. A "substantially pure" culture shall be deemed to include a culture of TFX-producing α-proteobacteria containing no other bacterial species in quantities sufficient to interfere with the replication or TFX production of the culture, or sufficient to be detected by normal bacteriological techniques. Plants in which the present invention may be applied will generally include those plants susceptible to crown gall disease, such as grape plants, fruit trees, and rose plants.

It is broadly intended within the scope of the present invention that the biocontrol agent will be applied to the plant, or inoculated into the soil with the plant or plant seeds so that a culture of the biocontrol agent will develop near or within the susceptible tissue of the plant as it grows. To facilitate this, it is preferred that the biocontrol agent, preferably diluted with a suitable extender or carrier, either be applied to the seeds or plants prior to planting or introduced into the furrows when the seeds or plants are planted. Alternatively, the biocontrol agent may be prepared with or without a carrier and sold as a separate inoculant to be applied directly to the plant or inserted directly into the furrows into which the seed or plant is planted. Such processes are generally well known in the art.

One advantageous technique may include applying the biocontrol agent to the plant or seeds through the use of a suitable coating mechanism or binder prior to the seeds or plants being sold into commerce for planting. The process of coating seeds and plants is generally well known to those skilled in the art. For example, the biocontrol agent may be mixed with a porous, chemically inert granular carrier as described by U.S. Pat. No. 4,875,921, which is incorporated herein by reference.

Whether or not the biocontrol agent is coated directly on the seed or plant, the biocontrol agent is preferably diluted with a suitable carrier or extender so as to make the culture easier to handle and to provide a sufficient quantity of material so as allow easy human handling. For example, a peat based carrier may be used as described by Bosworth et al, "Alfalfa yield response to inoculation with recombinant strains of *Rhizobium meliloti* carrying an extra copy of dct and/or modified nifA expression," *Appl. Environ. Microbiol.*, 60:3815–3832 (1994), incorporated herein by reference. In addition, it has been discovered that perlite, vermiculite and charcoal materials are suitable carrier substances. It is believed that many other non-toxic and biologically inert substances of dried or granular nature are also capable of serving as carriers for the biocontrol agent.

The density of inoculation of the biocontrol agent onto the plant or plant seed, or into the furrows, should be sufficient to populate the region of the seed or plant, or the sub-soil region adjacent to the roots of the seed or plant, with viable bacterial growth. An effective amount of biocontrol agent should be used. An effective amount is that amount sufficient to establish sufficient bacterial growth so that infection by crown gall inducing bacteria is inhibited or diminished as compared to infection by crown gall inducing bacteria in the absence of the biocontrol agent.

The project, results of which are described below, began as an effort to develop a strain of bacteria that could be used as a biocontrol agent for controlling crown gall disease in vine crops, such as grape. The thought was to introduce into an *Agrobacterium* species the ability to produce the TFX antibiotic so as to control tumorigenic *Agrobacterium* species that might otherwise prey upon susceptible plants. It was unknown at the initiation of this effort whether or not the TFX toxin would be effective within crown-gall susceptible plant tissue, as well as above ground environments exposed to sunlight, air, and other destabilizing agents. The toxin is normally found only in the rhizosphere of growing plants, which had been the only previous environment in which the TFX toxin had been demonstrated to be effective. We discovered that production of the TFX toxin can be successfully engineered into *Agrobacterium* species for use as a biocontrol agent to control the spread of tumorigenic *Agrobacterium* species within crown-gall susceptible tissue.

It was uncertain as to whether the species of *Agrobacterium* responsible for crown gall disease were susceptible to the TFX toxin. As described below, tests conducted to determine whether or not the *Agrobacterium vitis* strains were susceptible to TFX demonstrated that there was a level of susceptibility, but it was lower than might be expected upon previous TFX sensitivity measurements with other *Agrobacterium* species. In tests with *Rhizobium leguminosarum* T24 colonies only relatively small zones of inhibition were observed around the *Rhizobium* producing TFX. One Agrobacterium strain, biocontrol strain F2/5, was found to be TFX-resistant. Nevertheless, it was found that when the plasmid encoding the production of TFX was introduced into the *A. vitis* strain F2/5, an effective crown-gall biocontrol agent was created which was effective against most tumorigenic strains of *A. vitis* when co-inoculated with the tumorigenic strain. The biocontrol agent was found to be effective when the ratio of the biocontrol agent to the tumorigenic strains was at a ratio of 1 to 1 or higher.

Prior to this work it was also not clear whether TFX production would be effective at inhibiting galling by tumorigenic *Agrobacterium* in planta because TFX is rapidly degraded in situ. Previous studies have observed the degradation of antimicrobial peptides such as cecropin B and attacin E in plant apoplastic fluids. This was likely due to apoplastic proteinases. As a result, expression of antimicrobial peptides in plants had mixed results for enhancing disease resistance. For example, cecropin expression in transgenic tobacco did not confer resistance to *P. syringae* pv *tabaci*, likely due to low apoplastic peptide concentrations due to proteolysis. Jones and Kerr, "*Agrobacterium radiobacter* strain K1026, a genetically engineered derivative of strain K84 for biological control of crown gall", *Plant Disease* 73:15–18 (1989); Mills et al., "Evidence for the breakdown of cecropin B by proteinases in the intercellular fluid of peach leaves", *Plant Sci.* 104:17–22 (1999).

It was also believed that TFX production would be difficult to engineer in plants due to the complex mechanism by which active TFX is derived from tfxA. We discovered that *Agrobacterium rhizogenes* is capable of producing TFX by addition of the pT2TFXK plasmid containing the tfx operon but not tfuA. This discovery suggested that TFX production by crown gall biological control strains of *Agrobacterium*, such as *A. rhizogenes* K84 and *A. vitis* F2/5, may be enhanced by TFX production, and provide excellent delivery vehicles for TFX to the infection site.

There are additional benefits obtained by the production of the TFX toxin in the *A. vitis* strain F2/5. For example, biocontrol is extended to other non-grape vine hosts of *Agrobacterium*, such as *Nicotinia glauca*. The enhancement of the biocontrol F2/5 strain by virtue of the ability to produce TFX extends the ability of the F2/5 strain to control *A. vitis* strains on grapevine that it could not otherwise control without the ability to produce TFX. This result demonstrates that TFX production would enhance crown gall biocontrol for all other biocontrol strains, particularly of *Agrobacterium* strains, which can be used on other host plants. The ability to produce TFX in *Agrobacterium* offers the ability to confer biocontrol upon a strain as long as the producing strain is present in excess of the tumorigenic strain. High ratios of biocontrol to pathogen strain can easily be achieved in field situations by dipping the roots of planting stock in suspension of the biocontrol strain or by direct application of the bacterial suspensions of the biocontrol strain to the planting beds or to the plants themselves.

Thus, the ability to enhance the biocontrol status of *Agrobacterium* strains is not limited to particular exemplary strains of *Agrobacterium* described above and in the examples below. The results demonstrate that the TFX phenomenon of pathogen inhibition can be achieved in environments other than the rhizosphere and that the strategy works well in above ground environments. It thus becomes possible to transfer this toxin producing activity to any *Agrobacterium* strain sought to be used as a biocontrol agent. The plasmids described below are suitable and appropriate for introducing such activity into other crown gall forming bacterial strains, including other *Agrobacterium* strains.

While the examples set forth below are executed in *Agrobacterium vitis*, the same technique is anticipated to work in other crown gall forming bacterial strains, such as other strains of *Agrobacterium*. The examples below are intended to only be illustrative of the aspects of the present invention, and neither serve to limit or diminish the scope of the present invention.

EXAMPLES

Bacterial and plant growth conditions, strain construction

Bacterial strains investigated are listed in Table 1 below. The *A. vitis* strains (without pT2TFXK or pT2TX3K) were obtained from Dr. T. J. Burr, Cornell University. Bacteria were grown on BSM agar medium at 27° C. *A. vitis* F2/5(pT2TFXK) and F2/5(pT2TX3K) were constructed by triparental mating using standard procedures. Transconjugants were selected on BSM medium amended with 50 ppm kanamycin. Trimethoprim (10 ppm) was added to counterselect the *E. coli* donor and helper strains. Strains containing the plasmids pT2TFXK and pT2TX3K were grown for routine propagation on BSM amended with 50 ppm kanamycin. Prior to use in making inoculum suspensions for biological control assays these strains were grown overnight on BSM agar without kanamycin. The plasmids pT2TFXK and pT2TX3K both contain the full operon encoding the TFX peptide toxin, including genes tfxA through tfxG.

Plants (*Nicotiana glauca*) were grown in the greenhouse with supplemental illumination and fertilized as needed with a nutrient solution called CNS containing 2 mM $CaCl_2.2H_2O$, 0.5 mM $MgSO_4.7H_2O$, 2 mM KCl, 0.4 mM $KH_2PO_4$, 2.5 mM $NH_4N$ mM $FeSO_4.7H_2O$, 2.3 µM $H_3BO_3$, 0.9 µM $MnSO_4.H20$, 0.6 µM $ZnSO_4.7H_2O$ $NaMoO_4.2H_2O$, 0.11 µM $NiCl_2.6H_2O$, 0.01 µM $CoCl_2.6H_2O$, 0.15 µM CuSO

TABLE 1

Bacterial Strains

| Strain | Characteristics |
|---|---|
| Rhizobium | |
| T24 | |
| T24 Tn5::tfxB | |
| CE3 (pT2TFXK) | |
| CE3 (pT2TX3K) | |
| Agrobacterium vitis | |
| F2/5 | |
| F2/5 (pT2TFXK) | |
| F2/5 (pT2TX3K) | Plasmid contains tfxA deletion, non-Tfx |
| CG561 | Non-tumorigenic, non-biocontrol on grapevine |
| CG561 (pT2TFXK) | Contains Tfx-encoding plasmid, produces TFX |
| CG561 (pT2TX3K) | Plasmid contains tfxA deletion, non-Tfx producing strain |
| CG49 | Tumorigenic, nopaline-type pTi, controlled by F2/5 on grape |
| CG78 | Tumorigenic, vitopine-type pT1, not controlled by F2/5 coinoculation |
| K306 | Tumorigenic, octopine-type pT1, controlled by F2/5 on grape |
| CG106 | Tumorigenic |
| CG113 | Tumorigenic |
| CG435 | Tumorigenic |

In vitro antibiosis assay

*Agrobacterium vitis* strains (Table 1) were tested for sensitivity to trifolitoxin (TFX). Ten µl of the trifolitoxin-producing strain *Rhizobium leguminosarum* T24, or its Tfx-derivative, were spotted directly from frozen stocks onto BSM agar plates (Difco). The bacteria were allowed to grow for two to three days at 27° C. to allow TFX to accumulate in the medium. These plates were then sprayed with a light mist of either the highly-TFX sensitive *Rhizobium* 128Cl (positive control) or an *Agrobacterium vitis* test strain using a Preval spray gun (Precision Valve Company part #267).

Test-strain spray suspensions were made by suspending loops full of bacteria into 15 ml sterile distilled water until the suspension was barely visibly turbid. Sprayed plates were incubated for 2–4 days at 27° C. When growth of the test strain was apparent on the TFX non-producing strain plates, the plates were scored for zones of no growth around the TFX producing strain. Lack of a zone around the TFX non-producing strains indicated that zone formation was not due to factors other than TFX production. The same procedure was used with *Rhizobium* CE3 (pT2TFXK) and (PT2TX3K) as the TFX-producing and non-producing strains, respectively.

As expected based on previous results, the tested *Agrobacterium vitis* strains were sensitive to TFX-producing strains. However, the level of susceptibility was lower than predicted based upon previous TFX sensitivity measurements with CG-48 and CG-74. No zones of *A. vitis* growth inhibition were observed around *R. leguminosarum* T24 colonies, and only relatively small zones were observed around *R. etli* CE3(pT2TFXK), which produces more TFX than T24. Furthermore, one *A. vitis* strain, F2/5, was TFX-resistant.

Because *A. vitis* F2/5 produces an agrocin to which most of the tumorigenic strains are sensitive, the effect of TFX on *A. vitis* was assessed against TFX-producing and non-producing *Rhizobium* strains. None of the tested strains were sensitive to *R. leguminosarum* T24, which produces relatively low amounts of TFX. All of the *A. vitis* strains except for F2/5 were sensitive to *R. etli* CE3(pT2TFXK) as evidenced by zones of growth inhibition around the CE3 (pT2TFXK) colonies. *A. vitis* growth was not inhibited by a non-TFX metabolite or nutrient competition by CE3 (pT2TFXK) as evidenced by the lack of a zone around the near-isogenic tfxA mutant CE3(pT2TX3K) colony.

Evidence for TFX production by *A. vitis* strain F2/5 (pT2TFXK).

*A. vitis* strain F2/5 (pT2TFXK) was tested to determine if the strain was producing TFX. The assay was performed as described above with F2/5 (pT2TFXK) cultured in a single colony in the center of the plate. One day after growth at 28° C., the plates were sprayed with a dilute suspension of ANU794(pT2TX3K) or ANU794.

It was observed that strain F2/5(pT2TFXK) inhibited TFX-sensitive *R. leguminosarum* bv. *trifolii* ANU794 but had no effect on ANU794 following addition of the TFX resistance genes provided by pT2TX3K. Plasmids pT2TFXK and pT2TX3K confer resistance to TFX, tetracycline, and kanamycin with pT2TFXK also providing TFX production to a host strain. However, since strains F2/5 and F2/5(pT2TX3K) produced no zones of inhibition against ANU794 or ANU794(pT2TX3K), F2/5(pT2TFXK) is producing TFX.

In planta biological control of crown gall by TFX-producing strains

*Agrobacterium vitis* strains were suspended in sterile distilled water prior to the determination of colony forming units (CFU) per ml. These suspensions were adjusted to $OD_{650}$ 0.10 (approximately $10^8$ CFU/ml) using a Shimadzu UV-160 spectrophotometer and sterile distilled water, and stored until inoculation at 4° C. Actual inoculum viability and cell density were measured by dilution plating on BSM agar medium on the day that plants were inoculated.

Prior to inoculation, tumorigenic strains were diluted 10-fold with sterile distilled water to approximately $10^7$ CFU/ml. Biological control stocks were left undiluted, or diluted 10-fold (for CG49 and CG435 experiments) or 100-fold (for CG78 experiments). Thus, the CFU ratios were approximately 10:1, and 1:1 or 1:10 avirulent:tumorigenic strain. Immediately prior to plant inoculation tumorigenic strains were mixed 1:1 (vol:vol) with the appropriate biological control test strain. Positive controls were diluted 1:1 (vol:vol) with water. Thus, all plant inocula contained approximately $5\times10^6$ CFU/ml of the tumorigenic strains.

Plants (*Nicotiana glauca*) were inoculated by wounding the stem with a dissecting needle. Three or four inoculations were made per inoculum mixture on each of two plants. Thus, each of the two experiments included 6 to 8 repetitions per treatment. A 5 µl drop of bacterial suspension was placed on the wound and allowed to air dry. Inoculation sites were wrapped loosely with Parafilm (American National Can) for 1 week post-inoculation. Gall diameter perpendicular to the stem was measured 4 to 7 weeks post-inoculation using a caliper, and all measurements were included for statistical analysis. Results were analyzed using ANOVA at the $\alpha$=0.05 level of significance.

Figure 3:
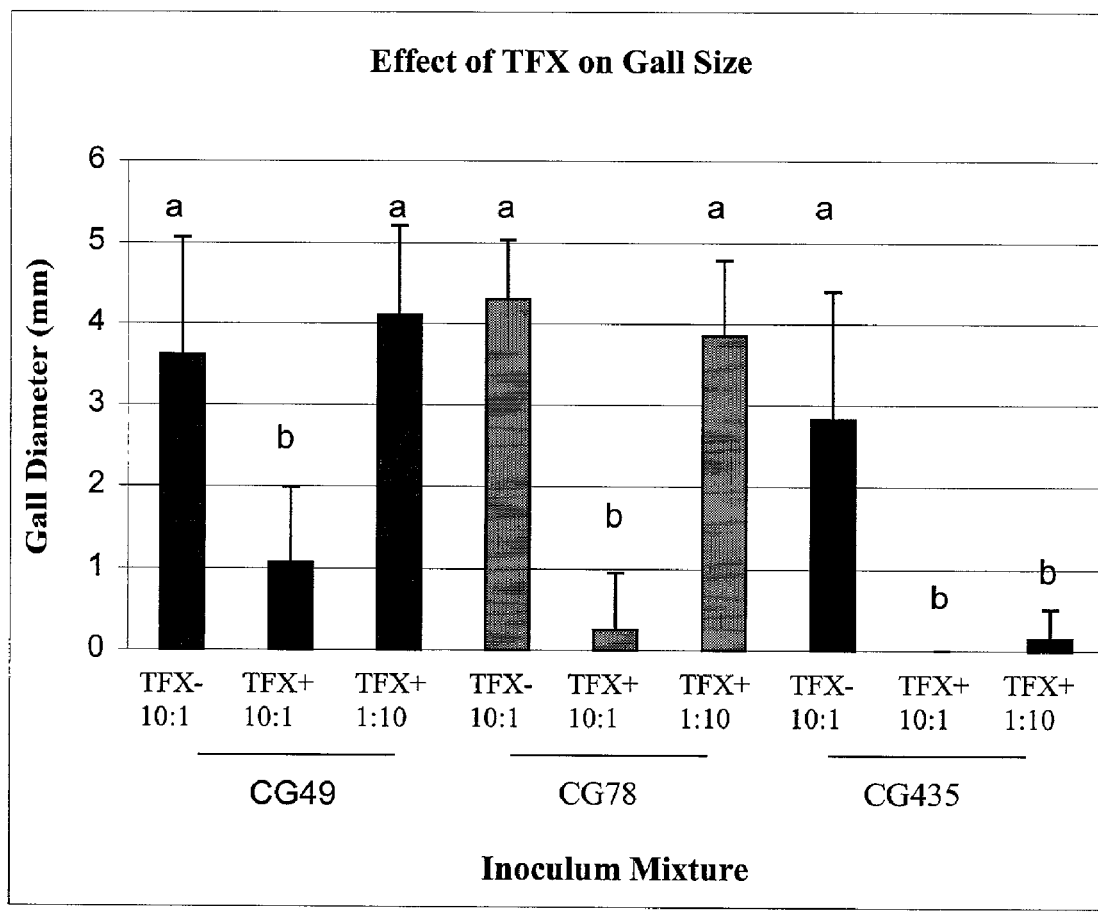
FIG. 3 graphically illustrates some of the results from the experiments described in the examples below.

As expected, F2/5 did not inhibit galling by tumorigenic *A. vitis* strains on *N. glauca*. A 10:1 ratio of *A. vitis* F2/5(pT2TFXK):pathogen caused a significant reduction in mean gall size relative to the TFX non-producing controls on *N. glauca* stems for all three tested tumorigenic strains. (FIG. 3.) High concentrations of F2/5(pT2TFXK) also reduced gall incidence for CG435 and CG78, but not for CG49. (Table 2.) A 1:1 ratio of F2/5(pT2TFXK):CG435 also resulted in a significant reduction in gall size and in gall incidence compared to controls. A 1:1 ratio of F2/5 (pT2TFXK):CG49 or F2/5(pT2TFXK):CG78 did not affect either incidence of galls or reduce gall size. Similarly, an excess (a 1:10 ratio) of any of the virulent strains to F2/5(pT2TFXK) resulted in a high incidence of disease and large gall size.

TABLE 2

Effect of (pT2TFXK) on Gall Incidence

| Biocontrol Strain | Tumorigenic Strain[a] | | |
| --- | --- | --- | --- |
| | CG49 | CG435 | CG78 |
| F2/5 | 6/6 | 6/6 | 6/6 |
| F2/5 (pT2TFXK) | 6/6 | 0/6 | 1/8 |

[a]Inoculations performed at 10:1 ratio of biocontrol:pathogenic strain. Presence of galls was scored visually by comparison to an uninoculated negative control one month post-inoculation.

Two principle benefits of TFX production by F2/5 were demonstrated. Biological control was extended to the non-grapevine host *N. glauca*, and biological control was extended to a strain that F2/5 failed to control (CG78) on grapevine. These effects are due to TFX production as demonstrated by the lack of efficacy of F2/5 against CG49, CG435, and CG78, and by the lack of efficacy of the near-isogenic TFX-non-producing F2/5(pT2TX3K) against CG78. TFX also provided biological control when the TFX-producing strain was present in excess of the tumorigenic strain. Thus, F2/5(pT2TFXK) effectively inhibited galling by all three tested tumorigenic strains when co-inoculated in approximately 10-fold excess.

At 1:1 or 1:10 inoculum ratios of F2/5(pT2TFXK):pathogen biological control was reduced or lost. This could be overcome by using high ratios of biological control:pathogen in the field, which should be easily achieved by dipping the roots of planting stock in suspensions of the biological control strain, or by directly applying the bacterial suspension to the planting bed.

TFX was also discovered to be inhibitory towards all tested species of *Agrobacterium*. These results suggested that TFX production would enhance crown gall biological control for other biological control strains, such as *A. rhizogenes* K84, and on other host plants, especially where a mixed inoculum of different tumorigenic *Agrobacterium* species occurs.

The effect of TFX production on gall size and the effective inoculum ratios are also illustrated graphically in FIG. 3. Gall diameter in millimeters perpendicular to the stem was measured one month post-inoculation. Wound sites were inoculated with 5 µl of mixed bacterial suspensions. Each inoculum mixture was inoculated into three wound sites on each of two plants, for a total of six inoculations per treatment.

We claim:

1. A method for controlling crown gall disease, said method comprising the steps of:
   (a) introducing onto a plant species susceptible to the disease an effective amount of a biologically pure culture of *Agrobacterium vitis* strain F2/5 genetically engineered to express a tfx operon, wherein the *Agrobacterium* enters the stem of the plant through a wound site on the plant, and wherein the *Agrobacterium* produces trifolitoxin which is capable of controlling crown gall disease on plants; and
   (b) observing control of crown gall disease on the plant compared to a plant not exposed to the trifolitoxin-producing *Agrobacterium*, wherein the plant is a grape or Nicotiana plant.

2. The method of claim 1 wherein the *Agrobacterium vitis* strain F2/5 comprises pT2TFXK, deposited as ATCC Patent Deposit Designation PTA-2356.

3. The method of claim 1 wherein the *Agrobacterium* is genetically engineered to express SEQ ID NO:1.

4. A method for controlling crown gall disease, said method comprising the steps of:
   (a) introducing onto a plant species susceptible to the disease an effective amount of a biologically pure culture of *Rhizobium* bacteria genetically engineered to express a tfx operon, wherein the *Rhizobium* enters the stem of the plant through a wound site on the plant, and wherein the *Rhizobium* produces trifolitoxin which is capable of controlling crown gall disease on plants; and
   (b) observing control of crown gall disease on the plant compared to a plant not exposed to the trifolitoxin-producing *Rhizobium*, wherein the plant is a grape plant.

5. The method of claim 4 wherein the *Rhizobium* is genetically engineered to express SEQ ID NO:1.

6. The method of claim 4 wherein the *Rhizobium* is genetically engineered to express a pT2TFXK plasmid.

7. A biocontrol agent for controlling crown gall disease comprising *Agrobacterium vitis* strain F 2/5 genetically engineered to express a tfx operon to produce trifolitoxin.

8. The biocontrol agent of claim 7 wherein the *Agrobacterium vitis* strain F2/5 comprises pT2TFXK, deposited as ATCC Patent Deposit Designation PTA-2356.

9. The biocontrol agent of claim 7 wherein the *Agrobacterium* is genetically engineered to express SEQ ID NO:1.

10. The method of claim 4 wherein the *Rhizobium* bacteria is *Rhizobium leguminosarum*.

* * * * *